(12) United States Patent
Arthur

(10) Patent No.: US 8,679,537 B2
(45) Date of Patent: *Mar. 25, 2014

(54) METHODS FOR SEALING AN ORIFICE IN TISSUE USING AN ALDOL-CROSSLINKED POLYMERIC HYDROGEL ADHESIVE

(75) Inventor: Samuel David Arthur, Wilmington, DE (US)

(73) Assignee: Actamaz Surgical Materials, LLC, Berkeley, CA (US)

( * ) Notice: Subject to any disclaimer, the term of this patent is extended or adjusted under 35 U.S.C. 154(b) by 1574 days.

This patent is subject to a terminal disclaimer.

(21) Appl. No.: 11/509,255

(22) Filed: Aug. 24, 2006

(65) Prior Publication Data

US 2007/0048251 A1 Mar. 1, 2007

Related U.S. Application Data

(60) Provisional application No. 60/710,923, filed on Aug. 24, 2005.

(51) Int. Cl.
*A61K 9/14* (2006.01)

(52) U.S. Cl.
USPC ........ 424/486; 424/484; 424/488; 424/78.08; 424/78.17; 424/78.31; 424/78.37; 424/78.38

(58) Field of Classification Search
USPC .................................................... 424/78.31
See application file for complete search history.

(56) References Cited

U.S. PATENT DOCUMENTS

| | | | |
|---|---|---|---|
| 3,029,187 A * | 4/1962 | Steinhardt et al. | 424/94.62 |
| 3,361,585 A * | 1/1968 | Armour et al. | 106/207.5 |
| 4,584,188 A | 4/1986 | Graham | |
| 4,708,821 A | 11/1987 | Shimokawa et al. | |
| 5,116,824 A | 5/1992 | Miyata et al. | |
| 5,162,430 A | 11/1992 | Rhee et al. | |
| 5,203,914 A | 4/1993 | Futami et al. | |
| 5,275,838 A | 1/1994 | Merrill | |
| 5,292,802 A | 3/1994 | Rhee et al. | |
| 5,308,889 A | 5/1994 | Rhee et al. | |
| 5,324,775 A | 6/1994 | Rhee et al. | |
| 5,328,995 A | 7/1994 | Schaulin et al. | |
| 5,505,952 A | 4/1996 | Jiang et al. | |
| 5,514,379 A | 5/1996 | Weissleder et al. | |
| 5,643,575 A | 7/1997 | Martinez et al. | |
| 5,733,563 A | 3/1998 | Fortier | |
| 5,874,500 A | 2/1999 | Rhee et al. | |
| 6,184,284 B1 | 2/2001 | Stokich, Jr. et al. | |
| 6,620,125 B1 | 9/2003 | Redl | |
| 2001/0056137 A1 | 12/2001 | Buter et al. | |
| 2002/0136769 A1 | 9/2002 | Kabanov et al. | |
| 2005/0002893 A1 * | 1/2005 | Goldmann | 424/70.27 |
| 2006/0078536 A1 | 4/2006 | Kodokian et al. | |
| 2006/0079599 A1 | 4/2006 | Arthur | |
| 2007/0048337 A1 | 3/2007 | Arthur | |

FOREIGN PATENT DOCUMENTS

| | | |
|---|---|---|
| FR | 2099308 | 4/1972 |
| JP | 1982-102932 | 6/1982 |
| JP | 58225542 | 12/1983 |
| JP | 61078883 | 4/1986 |
| JP | 1988-11167 | 1/1988 |
| JP | 05020458 | 3/1993 |
| JP | 6172727 | 6/1994 |
| JP | 10330572 | 12/1998 |
| JP | 2002348557 | 12/2002 |
| JP | 2003171637 | 6/2003 |
| JP | 2003171638 | 6/2003 |
| WO | WO 91/15368 | 10/1991 |
| WO | WO 97/22371 | 6/1997 |
| WO | WO 00/62827 | 10/2000 |
| WO | WO 01/16210 | 3/2001 |
| WO | WO 01/49268 | 7/2001 |
| WO | WO 03/020818 | 3/2003 |

OTHER PUBLICATIONS http://en.wikipedia.org/wiki/Super_glue.*
Kondo, et al., "Immobilization of Biocatalysts Using Crosslinked Acetoacetyl Poly(vinyl alcohol) Hydrogels", Hakko Kogaku Kaishi 69(5):337-344 (1991) Abstract only.
Pfannemuller, B., et al., "Chemical Modification of the Surface of the Starch Granules", Starch/Starke, vol. 95, No. 9, 1983, pp. 298-303.

* cited by examiner

*Primary Examiner* — James Rogers
(74) *Attorney, Agent, or Firm* — McCarter & English

(57) ABSTRACT

Methods for sealing an orifice in tissue in the body of a living animal using an adhesive formed by reacting an oxidized polysaccharide with a poly(hydroxylic) compound derivatized with acetoacetate groups in the presence of a base catalyst are disclosed. Methods for using the adhesive for medical and veterinary applications such as topical wound closure; and surgical procedures, such as intestinal anastomosis, vascular anastomosis, tissue repair, and ophthalmic procedures; and drug delivery are described.

27 Claims, No Drawings

METHODS FOR SEALING AN ORIFICE IN TISSUE USING AN ALDOL-CROSSLINKED POLYMERIC HYDROGEL ADHESIVE

This patent application claims the benefit of U.S. Provisional Patent Application No. 60/710,923, filed Aug. 24, 2005.

FIELD OF THE INVENTION

The invention relates to the field of medical adhesives. More specifically, the invention relates to methods for sealing an orifice in tissue in the body of a living animal using a polymer tissue adhesive formed by reacting an oxidized polysaccharide with a poly(hydroxylic) compound derivatized with acetoacetate groups in the presence of a base catalyst.

BACKGROUND OF THE INVENTION

Tissue adhesives have many potential medical applications, including topical wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the Fibrin-based adhesives do not covalently bind to the underlying tissue.

Several types of hydrogel tissue adhesives have been developed, which have improved adhesive and cohesive properties and are nontoxic. These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell or dissolve away too quickly, or lack sufficient adhesion or mechanical strength, thereby decreasing their effectiveness as surgical adhesives.

Kodokian et al., in copending and commonly owned U.S. patent application Ser. No. 11/244,756 (U.S. Patent Application Publication No. 2006/0078536), describe polymer tissue adhesives formed by reacting an oxidized polysaccharide with a water-dispersible, multi-arm polyether amine. The adhesives described in that disclosure overcome many of the limitations of hydrogel adhesives; however, the hydrogels are very fast curing so that they may not be optimal for some applications.

Arthur, in copending and commonly owned U.S. patent application Ser. No. 11/244,758 (U.S. Patent Application Publication No. 2006/0079599), describes polymer tissue adhesives formed by reacting poly(hydroxylic) compounds derivatized with acetoacetate groups and/or polyamino compounds derivatized with acetoacetamide groups with an amino-functional crosslinking compound. The adhesives described in that disclosure also overcome many of the limitations of hydrogel adhesives; however, the high concentrations of polyamines used may not be biocompatible to some tissues.

Futami et al. in U.S. Pat. No. 5,203,914 describe a dental impression composition which contains acetoacetylated polyvinyl alcohol, an aldehyde group-containing gelling agent, such as dialdehyde starch, and a filler, such as silica, alumina, and titanium oxide. A polymer tissue adhesive formed by reacting an oxidized polysaccharide with a poly (hydroxylic) compound derivatized with acetoacetate groups is not described in that disclosure.

Therefore, the problem to be solved is to provide a biocompatible tissue adhesive material having good adhesion to biological tissue, good cohesion, good mechanical strength, good aqueous and air stability, and a cure time that can be readily tailored to meet the needs of various applications.

Applicants have addressed the stated problem by discovering a polymer tissue adhesive formed by reacting an oxidized polysaccharide with a poly(hydroxylic) compound derivatized with acetoacetate groups in the presence of a base catalyst. The resulting adhesive has many desirable characteristics as a tissue adhesive and has a cure time that can be broadly controlled by adjusting the concentration of the base catalyst or by selecting base catalysts having different base strengths. Additionally, the adhesive is nontoxic to cells and non-inflammatory to tissue.

SUMMARY OF THE INVENTION

The invention provides a method for sealing an orifice in tissue in the body of a living animal using a polymer adhesive formed by reacting an oxidized polysaccharide with a poly (hydroxylic) compound derivatized with acetoacetate groups in the presence of a base catalyst. Accordingly, the invention provides a method for sealing an orifice in tissue in the body of a living animal comprising:

applying to the orifice
  (a) a first aqueous solution comprising from about 5% to about 40% by weight of a polysaccharide that has been oxidized to provide an oxidized polysaccharide that contains aldehyde groups, said polysaccharide having a molecular weight of about 1,000 to about 1,000,000 Daltons, and said oxidized polysaccharide having an equivalent weight per aldehyde group of about 90 to about 1500 Daltons, such that the oxidized polysaccharide has on average more than two aldehyde groups per chain, followed by
  (b) a second aqueous solution comprising from about 5% to about 40% by weight of a poly(hydroxylic) compound that has been derivatized to provide a derivatized poly(hydroxylic) compound that contains acetoacetate groups, said poly(hydroxylic) compound having a molecular weight of less than or equal to about 100,000 Daltons, and said derivatized poly(hydroxylic) compound having an equivalent weight per acetoacetate group of about 100 to about 2000 Daltons, such that the derivatized poly(hydroxylic) compound has on average more than two acetoacetate groups per molecule or
applying the second aqueous solution followed by the first aqueous solution and mixing the first and second aqueous solutions on the orifice, or
premixing the first and second aqueous solutions and applying the resulting mixture to the orifice before the resulting mixture completely cures,
thereby forming on said orifice a resorbable adhesive hydrogel, and allowing the hydrogel to remain on said orifice until said hydrogel is resorbed;
provided that:
  (i) at least one of the first aqueous solution or the second aqueous solution further comprises a base catalyst; or
  (ii) a base catalyst is applied to the orifice as a neat liquid or as part of a third aqueous solution, and said neat liquid or third aqueous solution is mixed with both the first aqueous and second aqueous solutions on the orifice or said neat liquid or third aqueous solution is premixed with both the first and second aqueous solutions, and the resulting mixture is subsequently applied to the orifice before the resulting mixture completely cures; or (iii) a combination of (i) and (ii).

In another embodiment, the invention provides a method for bonding at least two anatomical sites together comprising: applying to at least one of the at least two anatomical sites (a) a first aqueous solution comprising from about 5% to about 40% by weight of a polysaccharide that has been oxidized to provide an oxidized polysaccharide that contains aldehyde groups, said polysaccharide having a molecular weight of about 1,000 to about 1,000,000 Daltons, and said oxidized polysaccharide having an equivalent weight per aldehyde group of about 90 to about 1500 Daltons, such that the oxidized polysaccharide has on average more than two aldehyde groups per chain, followed by (b) a second aqueous solution comprising from about 5% to about 40% by weight of a poly(hydroxylic) compound that has been derivatized to provide a derivatized poly(hydroxylic) compound that contains acetoacetate groups, said poly(hydroxylic) compound having a molecular weight of less than or equal to about 100,000 Daltons, and said derivatized poly(hydroxylic) compound having an equivalent weight per acetoacetate group of about 100 to about 2000 Daltons, such that the derivatized poly(hydroxylic) compound has on average more than two acetoacetate groups per molecule, or applying the second aqueous solution followed by the first aqueous solution and mixing the first and second aqueous solutions on the at least one site, or premixing the first and second aqueous solutions and applying the resulting mixture to the at least one site before the resulting mixture completely cures, and contacting the at least two anatomical sites together; provided that:

(i) at least one of the first aqueous solution or the second aqueous solution further comprises a base catalyst; or (ii) a base catalyst is applied to the at least one site as a neat liquid or as part of a third aqueous solution, and said neat liquid or third aqueous solution is mixed with both the first aqueous and second aqueous solutions on said at least one site or said neat liquid or third aqueous solution is premixed with both the first and second aqueous solutions, and the resulting mixture is subsequently applied to the at least one site before the resulting mixture completely cures; or (iii) a combination of (i) and (ii).

Methods for using the polymer tissue adhesive of the invention for topical wound closure, intestinal and vascular anastomoses, sealing corneal incisions, and drug delivery are also provided.

DETAILED DESCRIPTION OF THE INVENTION

The invention relates to methods for sealing an orifice in tissue in the body of a living animal using a polymer adhesive formed by reacting an oxidized polysaccharide with a poly (hydroxylic) compound derivatized with acetoacetate groups in the presence of a base catalyst. Methods are disclosed for using the polymer adhesive of the invention as an adhesive for medical and veterinary applications including, but not limited to topical wound closure, and surgical procedures, such as intestinal anastomosis, vascular anastomosis, tissue repair, and ophthalmic procedures. The polymer adhesive may also have utility in drug delivery.

The following definitions are used herein and should be referred to for interpretation of the claims and the specification.

The term "oxidized polysaccharide" refers to a polysaccharide which has been reacted with an oxidizing agent to introduce aldehyde groups into the molecule.

The terms "dextran aldehyde" and "oxidized dextran" are herein used interchangeably to refer to dextran that has been reacted with an oxidizing agent to introduce aldehyde groups into the molecule.

The terms "equivalent weight per acetoacetate group", and "equivalent weight per aldehyde group" refer to the molecular weight of the compound divided by the number of acetoacetate or aldehyde groups, respectively, in the molecule.

The term "poly(hydroxylic) compound" refers to a chemical having more than two hydroxyl groups. The phrase "an orifice in tissue in the body of a living animal" refers to any orifice in tissue in the body of a living animal including, but not limited to, a wound, a surgical incision, or sutures or staples that have been applied to a wound or surgical incision in the tissue. The term "living animal" is meant to include living humans and animals.

The term "molecular weight" as used herein refers to the weight-average molecular weight.

The term "% by weight" as used herein refers to the weight percent relative to the total weight of the solution, unless otherwise specified.

The term "anatomical site" refers to any external or internal part of the body of humans or animals.

The term "tissue" refers to any tissue, both living and dead, in humans or animals.

The term "hydrogel" refers to a water-swellable polymeric matrix, consisting of a three-dimensional network of macromolecules held together by covalent or non-covalent crosslinks, that can absorb a substantial amount of water to form an elastic gel.

The term "resorbable hydrogel" refers to a hydrogel that dissolves and is eliminated from the body.

The term "comb polyether" refers to a polyether having a main chain with multiple trifunctional branch points from each of which a linear arm emanates.

The term "star polyether" refers to polyether having a single branch point from which linear arms emanate.

The term "water-dispersible" is used to describe chemical compounds which are water soluble or are able to be dispersed in water to form a colloidal suspension capable of reacting with a second reactant in aqueous solution.

By medical application is meant medical applications as related to humans and for veterinary purposes.

The invention provides methods for sealing an orifice in tissue in the body of a living animal using a tissue adhesive formed by reacting an oxidized polysaccharide with a poly (hydroxylic) compound derivatized with acetoacetate groups. The poly(hydroxylic) compound derivatized with acetoacetate groups undergoes a facile aldol condensation reaction with the oxidized polysaccharide in aqueous solution to form a hydrogel in the presence of a catalytic amount of base. The rate of aldol condensation, and hence the crosslinking rate, is a function of the base concentration and the base strength. Therefore, the cure time of the adhesive can be broadly tailored to meet the needs of various applications by adjusting the base concentration or by selecting base catalysts having different base strengths. The resulting polymer adhesive has many desirable characteristics as a tissue adhesive, including but not limited to, good adhesion to biological tissue, good cohesion, good mechanical strength, good aqueous and air stability, and is nontoxic to cells and non-inflammatory to tissue.

Oxidized Polysaccharides

Polysaccharides useful in the invention include, but are not limited to, dextran, chitin, starch, agar, cellulose, and hyaluronic acid. These polysaccharides are available commercially from sources such as Sigma Chemical Co. (St Louis, Mo.). In one embodiment, the polysaccharide is dextran. Suitable polysaccharides have a molecular weight from about 1,000 to about 1,000,000 Daltons, and in addition from about 3,000 to about 250,000 Daltons. In general, the use of polysaccharides with higher molecular weights results in hydrogels with greater strength, particular after prolonged soaking.

The polysaccharide is oxidized to introduce aldehyde groups using any suitable oxidizing agent, including but not limited to, periodates, hypochlorites, ozone, peroxides, hydroperoxides, persulfates, and percarbonates. In one embodiment, the polysaccharide is oxidized by reaction with sodium periodate, for example as described by Mo et al. (*J. Biomater. Sci. Polymer Edn.* 11:341-351, 2000). The polysaccharide is reacted with different amounts of periodate to give polysaccharides with different degrees of oxidation and therefore, different amounts of aldehyde groups, as described in detail in the General Methods Section of the Examples below. The aldehyde content of the oxidized polysaccharide may be determined using methods known in the art. For example, the dialdehyde content of the oxidized polysaccharide may be determined using the method described by Hofreiter et al. (*Anal Chem.* 27:1930-1931, 1955), as described in detail in the General Methods Section of the Examples below. In that method, the amount of alkali consumed per mole of dialdehyde in the oxidized polysaccharide, under specific reaction conditions, is determined by a pH titration. In one embodiment, the equivalent weight per aldehyde group of the oxidized polysaccharide is from about 90 to about 1500 Daltons, such that the oxidized polysaccharide has on average more than two aldehyde groups per chain. In general, the use of oxidized polysaccharides having higher equivalent weights results in lower crosslink density of the resulting hydrogel and slower cure rates. Additionally, the use of oxidized polysaccharides having lower equivalent weights typically gives adhesives having greater adhesive strength.

In the invention, the oxidized polysaccharide is used in the form of an aqueous solution, herein referred to as "the oxidized polysaccharide solution". The oxidized polysaccharide is added to water to give a concentration of about 5% to about 40% by weight, in addition from about 15% to about 30% by weight relative to the total weight of the solution. The optimal concentration to be used depends on the application and on the concentration of the acetoacetylated poly(hydroxylic) compound used, as described below, and can be readily determined by one skilled in the art using routine experimentation.

For use on living tissue, it is preferred that the aqueous solution comprising the oxidized polysaccharide be sterilized to prevent infection. Any suitable sterilization method known in the art that does not degrade the polysaccharide may be used, including, but not limited to, electron beam irradiation, gamma irradiation, ethylene oxide sterilization, or ultra-filtration through a 0.2 μm pore membrane.

The aqueous solution comprising the oxidized polysaccharide may further comprise various additives depending on the intended application. Preferably, the additive is compatible with the oxidized polysaccharide. Specifically, the additive does not contain primary or secondary amine groups that would interfere with the effective gelation of the hydrogel. The amount of the additive used depends on the particular application and may be readily determined by one skilled in the art using routine experimentation.

The aqueous solution comprising the oxidized polysaccharide may optionally include at least one thickener. The thickener may be selected from among known viscosity modifiers, including, but not limited to, polysaccharides and derivatives thereof, such as starch or hydroxyethyl cellulose.

The aqueous solution comprising the oxidized polysaccharide may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; cresol; chlorocresol; hydroquinone; sodium benzoate; potassium benzoate; triclosan and chlorhexidine.

The aqueous solution comprising the oxidized polysaccharide may also optionally include at least one colorant to enhance the visibility of the solution. Suitable colorants include dyes, pigments, and natural coloring agents. Examples of suitable colorants include, but are not limited to, FD&C and D&C colorants, such as FD&C Violet No. 2, D&C Green No. 6, D&C Green No. 5, D&C Violet No. 2; and natural colorants such as beetroot red, canthaxanthin, chlorophyll, eosin, saffron, and carmine.

The aqueous solution comprising the oxidized polysaccharide may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the aqueous solution comprising the oxidized polysaccharide may optionally include anti-inflammatory agents, such as indomethacin, salicylic acid acetate, ibuprophen, sulindac, piroxicam, and naproxen; thrombogenic agents, such as thrombin, fibrinogen, homocysteine, and estramustine; and radio-opaque compounds, such as barium sulfate and gold particles.

Poly(Hydroxylic) Compounds Derivatized with Acetoacetate Groups

A wide variety of poly(hydroxylic) compounds may be derivatized with acetoacetate groups to provide the water-soluble, derivatized poly(hydroxylic) compounds used in the invention. Typically, the weight-average molecular weight of useful poly(hydroxylic) compounds is less than or equal to about 100,000 Daltons. Suitable examples include, but are not limited to, poly(vinyl alcohol), partially-esterified poly (vinyl alcohol) such as for example, partially-hydrolyzed poly(vinyl acetate) still containing acetate groups as well as hydroxyl groups; poly(vinyl alcohol) copolymers, linear or branched polyethers, polysaccharides, monosaccharides, reduced monosaccharides, low molecular weight polyols, hydrolyzed polyvinyl acetate-methacrylate copolymers, polyether condensation products, and mixtures thereof.

In one embodiment, at least one poly(vinyl alcohol) is used as the poly(hydroxylic) compound that is derivatized with acetoacetate groups. Poly(vinyl alcohols) having different molecular weights and varying degrees of hydrolysis are available commercially from companies such as Sigma-Aldrich (St. Louis, Mo.). Poly(vinyl alcohols) suitable for use in the invention have a weight-average molecular weight of from about 1,000 Daltons to about 100,000 Daltons. Preferably, the weight-average molecular weight is from about 10,000 Daltons to about 50,000 Daltons, more preferably, from about 30,000 Daltons to about 50,000 Daltons. Useful polyvinyl alcohols have a degree of hydrolysis of from about 50% to about 100%-OH groups. The balance of groups are acetates. Preferably the degree of hydrolysis is from about 60% to about 100%, more preferably from about 80% to about 100%, most preferably from about 95% to about 99%.

In another embodiment, poly(vinyl alcohol) is used as the poly(hydroxylic) compound that is derivatized with acetoacetate groups in conjunction with dextran that is oxidized to provide aldehyde groups.

In another embodiment, at least one poly(vinyl alcohol) copolymer is used as the poly(hydroxylic) compound that is derivatized with acetoacetate groups. Suitable comonomers for the polyvinyl alcohol copolymers include, but are not limited to, ethylene, methyl acrylate, methyl methacrylate, acrylic acid, itaconic acid, maleic acid, fumaric acid, methyl vinyl ether, propylene, 1-butene, and mixtures thereof. Preferably, the copolymer comprises between about 1 mole percent and about 25 mole percent of the comonomer relative to the vinyl alcohol units. The acetoacetate derivative of the copolymer must be sufficiently water soluble to permit the preparation of an aqueous solution having a concentration of about 5% to about 40% by weight, as discussed below.

In another embodiment, at least one linear or branched polyether is used as the poly(hydroxylic) compound that is derivatized with acetoacetate groups. Useful linear or branched polyethers have a molecular weight of about 500 Daltons to about 20,000 Daltons. Suitable examples of linear or branched polyethers include, but are not limited to, linear or branched poly(ethylene oxide), linear or branched poly(propylene oxide), linear or branched copolymers of poly(ethylene oxide) and poly(propylene oxide), linear or branched poly(1,3-trimethylene oxide), linear or branched poly(1,4-tetramethylene oxide), star polyethers, such as star poly(ethylene oxide) and star poly(propylene oxide); comb polyethers such as comb poly(ethylene oxide) and comb poly(propylene oxide); and mixtures thereof. Many linear polyethers are available commercially from companies such as Sigma-Aldrich (St. Louis, Mich.). Many branched polyethers are available from Nektar Transforming Therapeutics (Huntsville, Ala.). Comb polyethers can be made by reacting ethylene oxide or propylene oxide or mixtures thereof with polyvinyl alcohol and a base.

In another embodiment, at least one polysaccharide is used as the poly(hydroxylic) compound that is derivatized with acetoacetate groups. The term "polysaccharide", as used herein, refers to a molecule comprising two or more monosaccharide units. Suitable polysaccharides include, but are not limited to, dextran, agar, alginic acid, hyaluronic acid, sucrose, maltose, lactose, raffinose, and mixtures thereof. The preferred weight-average molecular weight for the polysaccharide is from about 300 Daltons to about 200,000 Daltons, more preferably from about 500 Daltons to about 200,000 Daltons, most preferably from about 10,000 Daltons to about 100,000 Daltons.

In another embodiment, at least one monosaccharide is used as the poly(hydroxylic) compound that is derivatized with acetoacetate groups. Suitable monosaccharides include, but are not limited to, ribose, glucose, mannose, galactose, fructose, sorbose, and mixtures thereof.

In another embodiment, at least one reduced monosaccharide is used as the poly(hydroxylic) compound that is derivatized with acetoacetate groups. Suitable reduced monosaccharides include, but are not limited to, sorbitol, mannitol, iditol, dulcitol, and mixtures thereof.

In another embodiment, at least one low molecular weight polyol is used as the poly(hydroxylic) compound that is derivatized with acetoacetate groups. The polyol has more than two hydroxy groups and has a molecular weight of less than about 300 Daltons. Examples of useful low molecular weight polyols include, but are not limited to, glycerol, trimethylolpropane, pentaerythritol, dipentaerythritol and mixtures thereof.

In another embodiment, at least one hydrolyzed polyvinyl acetate-methyl acrylate copolymer is used as the poly(hydroxylic) compound that is derivatized with acetoacetate groups. Preferably, the methyl acrylate content of the hydrolyzed polyvinyl acetate-methyl acrylate copolymer is from about 1% to about 20% by weight of the copolymer and the polyvinyl acetate is 100% hydrolyzed. The hydrolyzed polyvinyl acetate-methyl acrylate copolymer of the invention has a molecular weight of about 20,000 Daltons to about 80,000 Daltons. An example of a useful poly(vinyl alcohol)-methyl acrylate copolymer is sold under the tradename Elvanol® 80-18 polyvinyl alcohol by E.I. du Pont de Nemours and Company (Wilmington, Del.).

In another embodiment, at least one polyether condensation product is used as the poly(hydroxylic) compound that is derivatized with acetoacetate groups. The condensation product is produced by reacting at least one core molecule having more than one carboxylic acid group with a sufficient amount of at least one polyether terminated with hydroxy groups to produce an esterified polyether with an average of more than two hydroxy end groups. Suitable core molecules include, but are not limited to oxalic acid, malonic acid, succinic acid, glutaric acid, adipic acid, benzenedicarboxylic acid, benzenetricarboxylic acid, benzenetetracarboxylic acid, cyclohexanetricarboxylic acid, cyclopentanetetracarboxylic acid, adamantanetetracarboxylic acid, biphenyltetracarboxylic acid, benzophenonetetracarboxylic acid, propanetricarboxylic acid, butanetetracarboxylic acid, and mixtures thereof. Suitable polyethers for use in the polyether condensation product include, but are not limited to linear poly(ethylene oxide), linear poly(propylene oxide), linear copolymers of poly(ethylene oxide) and poly(propylene oxide), linear poly(1,3-trimethylene oxide), and linear poly(1,4-tetramethylene oxide). The polyether condensation product may be prepared using methods known in the art. For example, a polyether condensation product may be formed by reacting polyethylene glycol with tetramethyl cyclopentane-1,2,3,4-tetracarboxylate. This is a general method that may be used to prepare other polyether condensation products.

Any of the aforementioned poly(hydroxylic) compounds may be derivatized with acetoacetate groups by reaction with diketene. As an example, the derivatization reaction for poly(vinyl alcohol) (PVOH) is as follows:

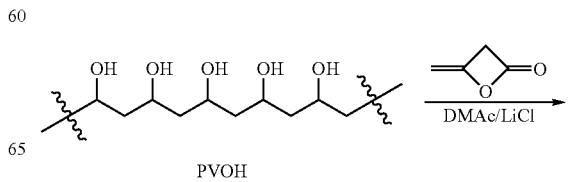

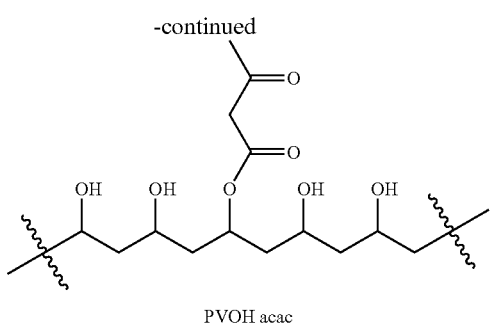

PVOH acac

Alternative methods of synthesis, such as ester exchange with t-butyl acetoacetate, are also available. Such alternative methods are within the scope of the present invention.

Preferably, the derivatized poly(hydroxylic) compounds of the invention have an equivalent weight per acetoacetate group of about 100 Daltons to about 2000 Daltons, such that the derivatized poly(hydroxylic) compounds have on average more than two acetoacetate groups per molecule. In general, the use of poly(hydroxylic) compounds derivatized with acetoacetate groups having higher equivalent weights results in a lower crosslink density of the resulting hydrogel and slower cure rates.

In the invention, the poly(hydroxylic) compound derivatized with acetoacetate groups is used in the form of an aqueous solution, herein referred to as "the acetoacetate solution". The aqueous solution comprises at least one poly(hydroxylic) compound derivatized with acetoacetate groups at a concentration of about 5% to about 40% by weight, more preferably from about 15% to about 30% by weight. The solution may comprise mixtures of any of the poly(hydroxylic) compounds derivatized with acetoacetate groups described above in order to modify the rate of gelation, the mechanical properties of the resulting hydrogel, biocompatibility, biodegradation rate and the like. If a mixture of different acetoacetate compounds is used, the total concentration of the components is from about 5% to about 40% by weight, preferably from about 15% to about 30% by weight (i.e., the water content of the aqueous solution is preferably from about 70% to about 85% by weight relative to the weight of the aqueous solution). The optimal concentration to be used depends on the application and on the concentration of the oxidized polysaccharide compound used. The cure rate of the hydrogel may be adjusted by controlling the ratio of the concentration of aldehyde groups on the oxidized polysaccharide to the concentration of acetoacetate groups on the poly(hydroxylic) compound. Ratios of approximately 1:1 result in faster cure rates. For the best adhesion to tissue, it is preferable that the ratio of aldehyde to acetoacetate reactive groups be greater than or equal to one.

For use on living tissue, it is preferred that the acetoacetate solution be sterilized to prevent infection. When the substitution level of the acetoacetate group on the polymer is less than or equal to 5 mole percent, the solution may be sterilized with gamma irradiation under a flux of 25 kilograys (kGy). Solutions of polymers having any substitution level of acetoacetate may be sterilized by autoclaving at about 121° C. or by ultrafiltration through a 0.2 μm pore membrane.

The acetoacetate solution of the invention may further comprise various additives depending on the intended application. The additive should be compatible with the acetoacetate component. Specifically, the additive does not contain primary amine groups that would interfere with effective gelation of the hydrogel. Any of the additives described above for the oxidized polysaccharide solution may be used.

Base Catalyst

A base is used to catalyze the aldol condensation reaction between the oxidized polysaccharide and the poly(hydroxylic) compound derivatized with acetoacetate groups to form the hydrogel adhesive of the invention. The base catalyst may be added to at least one of the oxidized polysaccharide solution or the acetoacetate solution. Preferably, the base catalyst is added to the oxidized polysaccharide solution because the acetoacetates may not be stable for long periods of time in a basic solution. Alternatively, the base catalyst may be added as a separate component either in a third aqueous solution or as a neat liquid. The base catalyst may be any basic chemical that raises the pH of the solution to a pH substantially above 5 and does not interfere with effective gelation of the hydrogel. The cure rate of the adhesive may be controlled by selecting base catalysts having different base strengths, as shown in Examples 61-79. Suitable base catalysts include, but are not limited to, sodium carbonate, sodium bicarbonate, trisodium phosphate, dibasic sodium phosphate, tetrasodium ethylenediaminetetraacetic acid (sodium EDTA), calcium carbonate, potassium carbonate, potassium bicarbonate, tripotassium phosphate, dibasic potassium phosphate, tetrapotassium ethylenediaminetetraacetic acid (potassium EDTA), and amines such as triethanolamine and imidazole. It should be understood that while strong bases such as sodium hydroxide, ammonium hydroxide, potassium hydroxide, sodium tetraborate, sodium methylthiolate and various alkylamines will efficiently catalyze the crosslinking of oxidized polysaccharides and poly(hydroxylic) compounds derivatized with acetoacetate groups, use in living systems will preclude using those bases possessing significant toxicity. For medical applications, the preferred base catalysts are the carbonate and phosphate salts, which are effective and biologically benign catalysts.

The concentration of the base catalyst may be used to tailor the cure rate of the adhesive. Higher base concentrations result in faster cure rates. Typically, the base is added to at least one of the oxidized polysaccharide solution, the acetoacetate solution, or a third aqueous solution to give a concentration between about 0.01% and about 1% by weight relative to the total weight of the solution.

If the base catalyst is added in the form of separate component for use on living tissue, it is preferred that the neat liquid or the aqueous solution comprising the base catalyst be sterilized to prevent infection. Any of the methods described above for the sterilization of the oxidized polysaccharide solution may be used.

If the base catalyst is used in the form of a third aqueous solution, the solution may further comprise various additives. Any of the additives described above for the oxidized polysaccharide solution, which are stable in a basic solution, may be used.

Termonomers

A third polymerizable component, co-reactive with the oxidized polysaccharide or the poly(hydroxylic) compound derivatized with acetoacetate groups, herein referred to as a termonomer, may be used in combination with the oxidized polysaccharide and the poly(hydroxylic) compound derivatized with acetoacetate groups to alter the properties of the hydrogel. For example, a hydrophobic polyether acetoacetate termonomer can be used to increase the hydrophobicity of the hydrogel, resulting in reduced water swelling and therefore longer persistence in the body. Alternatively, a hydrophilic polyether acetoacetate termonomer may be used to increase the hydrophilicity of the hydrogel, resulting in an increase in water swelling, and therefore higher hydrolytic degradation rates. Suitable termonomers include, but are not limited to, linear polyethers, such as ethylene glycol-propylene glycol-ethylene triblock polyethers, random ethylene glycol-propylene glycol polyethers, poly-1,3-propanediol, poly-1,4-butanediol; branched polyethers; water-dispersible hydroxyl-ended linear polyesters; water-dispersible hydroxyl-ended branched polyesters; star polyethers, such as a 4-arm or an 8-arm star polyethylene glycol; and partially-hydrolyzed poly(vinyl alcohol), which have been derivatized with acetoacetate groups. Many of these compounds are available commercially from companies such as Sigma-Aldrich (St. Louis, Mich.) and Nektar Transforming Therapeutics (Huntsville, Ala.) and may be derivatized with acetoacetate groups by reaction with diketene, as described above and as exemplified in Examples 35 to 40.

In the invention, the termonomer derivatized with acetoacetate groups is used in the form of an aqueous solution or dispersion. The termonomer derivatized with acetoacetate groups may be added to at least one of the acetoacetate solution, or the third aqueous solution comprising the base catalyst, or may be present in a separate fourth aqueous solution, herein referred to as "the termonomer solution". Whether the termonomer derivatized with acetoacetate groups is used as a component of the acetoacetate solution, the aqueous solution comprising the base catalyst, or is contained in a separate fourth aqueous solution, its concentration is from about 1% to about 25% by weight, relative to the weight of the solution.

For use on living tissue, it is preferred that the termonomer solution be sterilized to prevent infection. Any of the sterilization methods described above for the acetoacetate solution may be used.

The termonomer solution of the invention may further comprise various additives depending on the intended application. Any of the additives described above for the oxidized polysaccharide solution may be used. Additionally, the termonomer solution may also contain the base catalyst, described above.

Method of Application

In the method of the invention, the aqueous solution comprising the oxidized polysaccharide and the aqueous solution comprising the poly(hydroxylic) compound derivatized with acetoacetate groups are applied to an orifice in tissue in the body of a living animal. The orifice may be any orifice including, but not limited to, a wound, a surgical incision, or sutures or staples that have been applied to a wound or surgical incision in the tissue. The solutions may be applied to the orifice in any number of ways, as described below. Once both solutions are applied to the orifice in the presence of a base catalyst, they crosslink to form a resorbable hydrogel, a process referred to herein as curing, typically in about 10 seconds to about 3 minutes. Typically, the hydrogel is left in place until it is resorbed by the body.

In one embodiment, the two aqueous solutions, at least one of which further comprises a base catalyst, are applied to the orifice sequentially using any suitable means including, but not limited to, spraying, brushing with a cotton swab or brush, or extrusion using a pipet, or a syringe. The solutions may be applied in any order. Then, the solutions are mixed on the site using any suitable device, such as a cotton swab, a spatula, or the tip of the pipet or syringe.

In another embodiment, the two aqueous solutions, at least one of which comprises a base catalyst, are mixed manually before application to the orifice. The resulting mixture is then applied to the orifice before it completely cures using a suitable applicator, as described above.

In another embodiment, the two aqueous solutions, at least one of which further comprises a base catalyst, are contained in a double-barrel syringe. In this way the two aqueous solutions are applied simultaneously to the orifice with the syringe. Suitable double-barrel syringe applicators are known in the art. For example, RedI describes several suitable applicators for use in the invention in U.S. Pat. No. 6,620,125, (particularly FIGS. 1, 5, and 6, which are described in Columns 4, line 10 through column 6, line 47) which is incorporated herein by reference. Additionally, the double barrel syringe may contain a motionless mixer, such as that available from ConProtec, Inc. (Salem, N.H.) or MixPac Systems AG (Rotkreuz, Switzerland), at the tip to effect mixing of the two aqueous solutions prior to application.

In another embodiment wherein a third component comprising a base catalyst, either as a neat liquid or in a third aqueous solution, is used, the three solutions are applied to the orifice in any order using any of the methods described above and the solutions are well-mixed on the site. In this embodiment, the double-barrel syringe may be modified to have three barrels, one for each of the solutions. Alternatively, the three solutions may be premixed as described above, and the resulting mixture is then applied to the orifice before it completely cures using a suitable applicator, as described above.

In another embodiment wherein a separate aqueous solution comprising a termonomer is used, the three solutions, at least one of which further comprises a base catalyst, are applied to the orifice in any order using any of the methods described above and the solutions are well-mixed on the site. In this embodiment, the double-barrel syringe may be modified to have three barrels, one for each of the solutions. Alternatively, the three solutions may be premixed as described above, and the resulting mixture is then applied to the orifice before it completely cures using a suitable applicator, as described above.

Alternatively, the methods described above can be performed by applying four solutions, the oxidized polysaccharide solution, the acetoacetate solution, a third component comprising a base catalyst, either as a neat liquid or in a third aqueous solution, and a fourth aqueous solution comprising a termonomer to an orifice in tissue in the body of a living animal. In this embodiment, the four solutions are applied to the orifice separately in any order and mixed, or are premixed and applied to the orifice before the resulting mixture completely cures, as described above.

In another embodiment, the tissue adhesive of the invention is used to bond at least two anatomical sites together. In this embodiment, a the two aqueous solutions, at least one of which further comprises a base catalyst, is applied to at least one site and the solutions are mixed on the site, or the solutions are either premixed manually or using a double-barrel syringe applicator and applied to at least one of the anatomical sites to be bonded, as described above. The two or more sites are contacted and held together manually or using some other means, such as a surgical clamp, for a time sufficient for the mixture to cure.

In another embodiment wherein a third component comprising a base catalyst, either as a neat liquid or in a third aqueous solution, is used along with the oxidized polysaccharide solution and the acetoacetate solution to bond at least two anatomical sites together, each of the three solutions is applied to at least one anatomical site in any order and the solutions are well-mixed on the site. Alternatively, the three solutions are premixed using any of the methods described above, and the resulting mixture is applied to at least one of the anatomical sites to be bonded before the mixture completely cures. The two or more sites are then contacted and held together manually or using some other means, such as a surgical clamp, for a time sufficient for the mixture to cure.

In another embodiment wherein an aqueous solution comprising the termonomer is used along with the oxidized polysaccharide solution and the acetoacetate solution to bond at least two anatomical sites together, each of the three solutions, at least one of which further comprises a base catalyst, is applied to at least one anatomical site in any order and the solutions are well-mixed on the site. Alternatively, the three solutions are premixed using any of the methods described above, and the resulting mixture is applied to at least one of the anatomical sites to be bonded before the mixture completely cures. The two or more sites are then contacted and held together manually or using some other means, such as a surgical clamp, for a time sufficient for the mixture to cure.

Alternatively, the methods described above can be performed by applying four solutions, the oxidized polysaccharide solution, the acetoacetate solution, a third component comprising a base catalyst, either as a neat liquid or in a third aqueous solution, and a fourth aqueous solution comprising a termonomer to an anatomical site to bond two or more sites together. In this embodiment, the four solutions are applied to the anatomical site separately in any order and mixed on the site, or are premixed and applied to the site before the resulting mixture completely cures, as described above. The two or more sites are then contacted and held together manually or using some other means, such as a surgical clamp, for a time sufficient for the mixture to cure.

Medical and Veterinary Applications:

The tissue adhesive of the invention has many potential medical and veterinary applications, including, but not limited to, topical wound closure, surgical procedures, such as intestinal anastomosis, vascular anastomosis, and ophthalmic procedures; and drug delivery. For these uses, procedures involving the application of two aqueous solutions, one comprising the oxidized polysaccharide and the other comprising the poly(hydroxylic) compound derivatized with acetoacetate groups, at least one of which further comprises a base catalyst, are described below. The application of three solutions or four solutions wherein the third solution comprises a base catalyst, and the fourth solution comprises a termonomer may also be used for these purposes using the procedures described above.

The tissue adhesive of the invention may be used for treatment of topical wounds, including but not limited to, minor cuts, scrapes, irritations, abrasions, lacerations, burns, sores, and surgical wounds. For topical wound closure, the oxidized polysaccharide solution and the acetoacetate solution are applied to the wound using the methods described above, and the mixture is allowed to cure.

The tissue adhesive of the invention may also be used in surgical procedures, including but not limited to, intestinal anastomosis, vascular anastomosis, and ophthalmic procedures, such as sealing corneal cataract incisions.

Intestinal anastomosis is a surgical procedure that is well known to skilled surgeons. The procedure, which involves joining two segments of the intestine together after a resection, is described by Sweeney et al. (*Surgery* 131:185-189, 2002). The two segments of the intestine are joined together using sutures or staples. A problem encountered with this procedure is leakage around the sutures or staples. Leakage rates of 5-8% have been reported (Bruce et al. *Br. J. Surg.* 88:1157-1168, 2001). The tissue adhesive of the invention may be used to supplement the sutures or staples used in intestinal anastomoses, providing a better seal that reduces leakage. In this application, the oxidized polysaccharide solution and the acetoacetate solution are applied to the intestine around the sutures or staples, using the methods described above, and the mixture is allowed to cure.

Additionally, the tissue adhesive of the invention may be used in vascular anastomosis procedures. This procedure is similar to intestinal anastomosis, described above, and is used for vascular grafts. The two segments of the blood vessel are joined together using sutures or staples. The tissue adhesive of the invention may be used to supplement the sutures or staples, providing a better seal that reduces leakage. In this application, the oxidized polysaccharide solution and the acetoacetate solution are applied to the blood vessel around the sutures or staples, using the methods described above, and the mixture is allowed to cure.

Temporal clear corneal incisions and scleral tunnel incisions are used during cataract surgery. These procedures are well known to the skilled cataract surgeon. Although these incisions can be sealed with sutures, many surgeons prefer sutureless, self-sealing incisions. However, problems arise with leakage through the sutureless incisions, causing endophthalmitis (Sarayba et al. Amer. *J. Opthamol.* 138:206-210, 2004, and Kim et al. *J. Cataract Refract. Surg.* 21:320-325, 1995). The tissue adhesive of the invention may be used to seal both clear corneal incisions and scleral tunnel incisions to prevent leakage. In this application, the oxidized polysaccharide solution and the acetoacetate solution are applied to the site of the incision in the eye, using the methods described above, and the mixture is allowed to cure. Additionally, the two aqueous solutions may be coated on the sides of the scalpel blade used to make the incision, one solution on each side of the blade, to apply them to the site when the site is ready for closure.

The tissue adhesive of the invention may also be used for drug delivery to a selected anatomical site. In this application, at least one of the aqueous solutions further comprises a pharmaceutical drug or therapeutic agent. Suitable pharmaceutical drugs and therapeutic agents are well known in the art. An extensive list is given by Kabonov et al. in U.S. Pat. No. 6,696,089, which is incorporated herein by reference (in particular, columns 16 to 18). Examples include, but are not limited to, antibacterial agents, antiviral agents, antifungal agents, anti-cancer agents, vaccines, radiolabels, anti-inflammatories, anti-glaucomic agents, local anesthetics, anti-neoplastic agents, antibodies, hormones, and the like. In this application, oxidized polysaccharide solution and the acetoacetate solution, at least one of which further comprises the pharmaceutical drug or therapeutic agent of interest, are applied to the desired anatomical site using the methods described above. After the hydrogel cures, the drug or therapeutic agent is released to the desired anatomical site. The rate of release depends on the crosslink density of the hydrogel, which can be controlled by the extent of crosslinking, which in turn is determined by the concentrations of the oxidized polysaccharide and the acetoacetylated poly(hydroxy) compound used, as well as the relative levels of functional groups present on these respective reactants. The concentration of reagents needed to obtain the proper rate of drug release for any particular application can be readily determined by one skilled in the art using routine experimentation.

Additionally, the tissue adhesive of the invention may be useful for other medical applications. These applications include, but are not limited to, an adhesive to hold an implant in place, an adhesive used on tissue to block air, moisture, fluid or microbial migration, and an adhesive to supplement sutures or staples in other surgical procedures, such as cholecystectomy, ostomy port, appendectomy, bariatrics, retinal reattachment, Cesarean closure, abdominal hysterectomy, and the closure of trauma punctures, and ruptured membranes.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "meq" means milliequivalent(s), "PVOH" means polyvinyl alcohol, "acac" means acetoacetate, "PVOH acac" means polyvinyl alcohol acetoacetate, "eq wt" means equivalent weight, "$M_w$" means weight-average molecular weight, "$M_n$" means number-average molecular weight, "wt %" means percent by weight, "mol %" means mole percent, "Vol" means volume, "EO" means ethylene oxide, "PO" mean propylene oxide; "PEG" means polyethylene glycol, "Da" means Daltons, "kDa" means kiloDaltons, "MWCO" means molecular weight cut-off, "kPa" means kilopascals, "psi" means pounds per square inch, "UV" means ultraviolet, and a reference to "Aldrich" or a reference to "Sigma" means the said chemical or ingredient was obtained from Sigma-Aldrich, St. Louis, Mo.

General Methods:
Reagents:

Dextran ($M_w$=10,000) was purchased from Sigma-Aldrich (St Louis, Mo.). Sodium periodate (99% purity, CAS No. 7790-28-5) was purchased from Acros Organics (Morris Plains, N.J.). All other reagents were obtained from Sigma-Aldrich unless otherwise noted.

Preparation of Oxidized Dextran:

The following procedure was used to prepare an oxidized dextran, also referred to herein as dextran aldehyde, with about 48% aldehyde content conversion from dextran having a molecular weight of 10,000 Daltons. A similar procedure was used for dextrans having a molecular weight of 20,000, and 40,000 Daltons. Other aldehyde conversions were obtained by varying the concentration of the periodate solution used.

Dextran ($M_w$=10,000; 19.0 g) was added to 170 g of distilled water (10 wt % aqueous solution) in a 500 mL round bottom flask. The solution was stirred for 15 to 30 min. Then, 17.7 g of sodium periodate in 160 g of distilled water (10 wt % aqueous solution) was added to the dextran solution all at once. The mixture was stirred at room temperature for 5 h. After this time, the solution was removed from the round bottom flask, divided into four equal volumes and dispensed into 4 dialysis membrane tubes (molecular weight cut-off of 3500 Daltons). The dialysis tubes were dialyzed in deionized water for 4 days. During this dialysis, the water was changed twice each day. The aqueous samples were removed from the dialysis membrane tubes, frozen in wide-mouth polyethylene containers using liquid nitrogen, and lyophilized to afford a white fluffy product The dialdehyde content in the resulting oxidized dextran was determined using the following procedure. The oxidized dextran (0.1250 g) was added to 10 mL of 0.25 M NaOH in a 250 mL Erlenmeyer flask. The mixture was gently swirled and then placed in a temperature-controlled sonicator bath at 40° C. for 5 min until all the material dissolved, giving a dark yellow solution. The sample was removed from the bath and immediately cooled under cold tap water for 5 min. Then, 15.00 mL of 0.25 M HCl was added to the solution, followed by the addition of 50 mL of distilled water and 1 mL of 0.2% phenolphthalein solution. This solution was titrated with 0.25 M NaOH using a 50 mL buret and the endpoint was determined by a color change from yellow to purple/violet. The same titration was carried out on a sample of the starting dextran.

The dialdehyde content, also referred to herein as the oxidation conversion, in the oxidized dextran sample was calculated using the following formula:

$$\text{Dialdehyde Content} = \frac{(Vb - Va)_s}{W_s/M} - \frac{(Vb - Va)_p}{W_p/M} \times 100 \ (\%)$$

Vb=total meq of base
Va=total of meq of acid
W=dry sample weight (mg)
M=molecular weight of repeating unit=162
s=the oxidized sample
p=the original sample Preparation of Polyvinyl Alcohol Acetoacetate

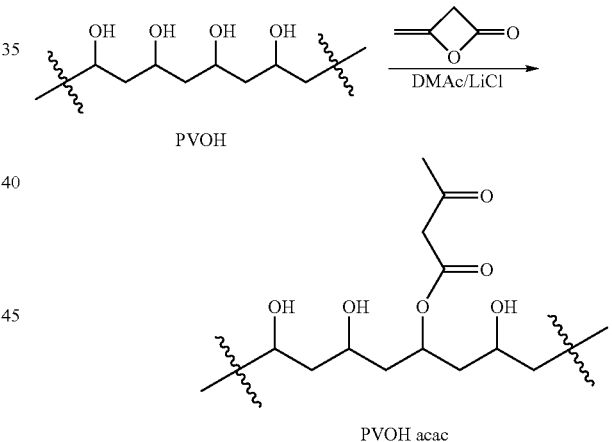

A mixture of dried (70° C. vacuum oven for 12 h; 350 mm Hg/nitrogen sweep) polyvinyl alcohol (25.0 g Aldrich #36, 313-8; $M_w$=31000-50000; 570 mmol OH), anhydrous lithium chloride (3 g), N,N-4-dimethylaminopyridine (0.10 g) and dry dimethylacetamide (150 mL) was stirred in a 500-mL round bottom flask in a 90° C. oil bath under nitrogen for 1 h to give a hazy, colorless solution. Then, the solution was cooled to 70° C. and stirred as 7.5 mL (8.2 g; 97 mmol) of 85% diketene (Aldrich #42,236-3) was added over a period of 20-30 sec. The resulting orange solution was stirred at 70-75° C. for 2 h (the mixture went up to 80° C. briefly just after diketene addition). Then, the polymer solution was added with stirring to a mixture containing 250 mL of methanol and 750 mL of acetone in a Waring blender. The solvent was vacuum-filtered off the gummy polymer suspension. The polymer was blended with 700 mL of fresh acetone and the resulting suspension was filtered. The polymer was dried under a nitrogen blanket to yield 27.6 g of polyvinyl alcohol acetoacetate. 1H NMR ($D_2O$): by ratio of the 2.33-ppm acac $CH_3$ peak to the 1.7-ppm backbone methylene hydrogen ($H_2CCHOH$) peak the polymer contained 10.6 mol % acetoacetate groups (eq wt=500).

The product was dissolved in 250 mL of autoclaved water and the solution was clarified by pressure filtration through a Millipore cellulose prefilter (Millipore Corp., Billerica, Mass.) followed by dialysis in a Spectra/Por 3.5 kDa MWCO membrane (Spectrum Laboratories, Inc., Rancho Domingas, Calif.) against running deionized water for 60 h. The solution was then lyophilized to yield dry, fluffy polyvinyl alcohol acetoacetate.

1H NMR ($D_2O$): 11.0 mol % acetoacetate groups (eq wt=485).

The acetoacetate content of the polyvinyl alcohol can be varied by varying the amount of diketene used.

Examples 1 and 2

Preparation of Dextran Aldehyde-Polyvinyl Alcohol Acetoacetate Hydrogels

The purpose of these Examples was to prepare and characterize dextran aldehyde-polyvinyl alcohol acetoacetate hydrogels. The hydrogels were prepared by reacting dextran aldehyde and polyvinyl alcohol acetoacetate in the presence of sodium carbonate as a base catalyst.

Preparation of Hydrogels:

The following solutions were prepared and used to make hydrogels:

1A 25 wt % dextran aldehyde ($M_w$=10 kDa; 48% conversion; eq wt=160);
1B 19 wt % PVOH acac ($M_w$=31-50 kDa; eq wt=440)+1 wt % sodium carbonate;
1C 19 wt % PVOH acac ($M_w$=31-50 kDa; eq wt=600)+1 wt % sodium carbonate.

Hydrogel disks were prepared by mixing the dextran aldehyde solution, contained in a 2 mL syringe, with the PVOH acac solutions, contained in 1 mL syringes, as shown in Table 1, using a syringe Y-mixer with a 13-stage static mixing tip (ConProtec, Inc., Salem, N.H.). The syringe-mixed liquid was quickly extruded from the mixer tip into 13-mm circular silicone rubber molds about 4 mm deep. Gelation occurred within 20 sec of mixing. The hydrogel disks were allowed to cure at room temperature for 15 min before storing in plastic bags.

TABLE 1

Solutions Used to Prepare Hydrogels

| Example | Dextran Aldehyde Solution | PVOH acac Solution | Acac/Aldehyde Mole Ratio |
|---|---|---|---|
| 1 | 1A | 1B | 0.91 |
| 2 | 1A | 1C | 0.66 |

Characterization of Hydrogel Disk Properties:

The mechanical properties and the swelling properties of the hydrogel disks were evaluated using the following tests. The flexibility was tested by bending the disk double between finger and thumb. Bending was a severe test, as the disk diameter/height ratio was less than 5. Then, a second disk was stretched by hand until it broke, again between finger and thumb, to obtain a rough estimate of extension to break. The relative stiffness of the rubbery hydrogels was characterized as follows:

stiff: comparable to a gum eraser;
firm: comparable to cured acrylic caulk;
soft: comparable to a Jello™ "jiggler" or foamed rubber.

A very rough correlation of these designations with the Shore A hardness scale is as follows:

Stiff: Shore A~30
Firm: Shore A~10-20
Soft: Shore A<5

The results are given in Table 2.

TABLE 2

Results of Mechanical Tests of Hydrogels

| Example | Appearance of Hydrogel | Snap on Bending | Stretch to Break |
|---|---|---|---|
| 1 | Soft rubber | 90° | <10% |
| 2 | Firm rubber | <90° | 10% |

The swelling properties of the hydrogels were evaluated in the following manner. One disk of each composition was weighed and then allowed to stand in a scintillation vial with 10 mL of deionized water at 25° C. for 21 h. The disks were taken out, patted dry and re-weighed. The fractional water swell was calculated using the formula:

$$\text{water swell} = (\text{swollen wt/as-made wt}) - 1.$$

The hydrogels contained about 80 wt % water as made.

As-made hydrogel disks were water-swollen for 20-24 h, weighed, and then dehydrated by heating in a vacuum oven (20 inches of mercury (67.7 kPa) vacuum) at 120° C. under a nitrogen bleed for 20 h and reweighed to determine swollen water content. The equilibrium water swell (Q) was calculated using the formula:

$$Q = (\text{swollen wt})/(\text{dry wt}).$$

The mechanical properties of the swollen gels were evaluated as described above. The results of the swelling tests are given in Table 3.

TABLE 3

Results of Swelling Tests

| Example | Appearance | Stretch to Break | Snap on Bending | Water Swell | Q |
|---|---|---|---|---|---|
| 1 | Soft rubber | <10% | 90° | 0.28 | 6.0 |
| 2 | Firm rubber | <10% | 90° | 0.36 | 6.7 |

Examples 3-11

Preparation of Dextran Aldehyde-Polyvinyl Alcohol Acetoacetate Hydrogels with Different Swelling Properties The purpose of these Examples was to prepare dextran aldehyde-polyvinyl alcohol acetoacetate hydrogels having different swelling properties by using dextran aldehyde having different oxidation conversions and PVOH acac with different equivalent weights.

Preparation of Hydrogels:

The following solutions were prepared and used to make hydrogels:

2A 25 wt % dextran aldehyde ($M_w$=10 kDa; 48% conv; eq wt=160)
2B 25 wt % dextran aldehyde ($M_w$=10 kDa; 35% conv; eq wt=210)
2C 25 wt % dextran aldehyde ($M_w$=10 kDa; 23% conv; eq wt=330)
2D 19 wt % PVOH acac ($M_w$=31-50 kDa; eq wt=600)+0.25 wt % $Na_2CO_3$
2E 19 wt % PVOH acac ($M_w$=31-50 kDa; eq wt=740)+0.25 wt % $Na_2CO_3$
2F 19 wt % PVOH acac ($M_w$=31-50 kDa; eq wt=925)+0.25 wt % $Na_2CO_3$.

Hydrogel disks were prepared as follows. The Luer end was cut off a disposable 10-mL plastic syringe. The plunger was withdrawn about 1 inch (2.5 cm) from the open end, and a silicone rubber disk having the same diameter as the barrel was inserted on top of the syringe plunger to provide a flat, non-stick surface. The syringe was clamped vertically in a vise and the dextran aldehyde solution (60 μL) and the PVOH acac solution (0.30 mL), as shown in Table 4, were quickly added to the syringe barrel on top of the silicone rubber disk insert and were mixed well with a small spatula for about 10 sec. The syringe was allowed to stand for 5 min as the mixture cured. The finished hydrogel disk was then carefully pushed out with the plunger and placed in a small plastic bag.

TABLE 4

Solutions Used to Prepare Hydrogels

| Example | Dextran Aldehyde Solution | PVOH acac Solution | Acac/Aldehyde Mole Ratio |
|---|---|---|---|
| 3 | 2A | 2D | 1.0 |
| 4 | 2B | 2D | 1.3 |
| 5 | 2C | 2D | 2.1 |
| 6 | 2A | 2E | 0.8 |
| 7 | 2B | 2E | 1.1 |
| 8 | 2C | 2E | 1.7 |
| 9 | 2A | 2F | 0.7 |
| 10 | 2B | 2F | 0.9 |
| 11 | 2C | 2F | 1.4 |

Characterization of Hydrogel Disk Properties:

The mechanical properties and the swelling properties of the hydrogel disks were evaluated using the tests described in Examples 1 and 2. The results of the testing are provided in Tables 5 and 6.

TABLE 5

Results of Mechanical Tests of Hydrogels

| Example | Appearance of Hydrogel | Snap on Bending | Stretch to Break |
|---|---|---|---|
| 3 | Firm rubber | 90° | 10% |
| 4 | Firm rubber | 180° | 10% |
| 5 | Firm rubber | >90° | 10% |
| 6 | Firm rubber | >90° | 10% |
| 7 | Firm rubber | >90° | 10% |
| 8 | Firm rubber | 180° without breaking | 10% |
| 9 | Firm rubber | 180° | 10% |
| 10 | Firm rubber | 180° | 10% |
| 11 | Firm rubber | 180° | 10% |

TABLE 6

Results of Swelling Tests

| Example | Appearance | Stretch to Break | Snap on Bending | Water Swell | Q |
|---|---|---|---|---|---|
| 3 | Firm rubber | 10% | 180° | 0.25 | 6.0 |
| 4 | Firm rubber | 10% | 90° | 0.43 | 7.0 |
| 5 | Firm rubber | 10% | 90° | 0.82 | 9.0 |
| 6 | Firm rubber | 10% | 90° | 0.54 | 7.7 |
| 7 | Firm rubber | 10% | 180° | 0.65 | 8.0 |
| 8 | Soft rubber | 10% | 180° | 0.98 | 10.1 |
| 9 | Firm rubber | 10% | 180° | 0.48 | 7.3 |
| 10 | Soft rubber | 10% | 90° | 0.91 | 9.0 |
| 11 | Soft rubber | 10% | 180° | 1.09 | 10.1 |

From the Q values and the swelling values, it can be seen that the crosslink density may be controlled by varying the equivalent weights of the reactants.

The hydrogel disks were then soaked in phosphate buffer (pH=7.4) for 7 days and the mechanical properties were retested. The results of the testing are given in Table 7. The results demonstrate that the hydrogels maintain their mechanical properties after extended exposure to buffer solution.

TABLE 7

Results of Mechanical Tests of Soaked Hydrogels

| Example | Appearance of Hydrogel | Stretch to Break | Snap on Bending |
|---|---|---|---|
| 3 | Firm rubber | <10% | 180° |
| 4 | Firm rubber | <10% | 180° |
| 5 | Soft rubber | >10% | 180° |
| 6 | Firm rubber | <10% | >90° |
| 7 | Firm rubber | 10% | 180° |
| 8 | Soft rubber | 10% | 180° |
| 9 | Firm rubber | 10% | 180° |
| 10 | Soft rubber | 10% | 180° |
| 11 | Soft rubber | 10% | 180° |

Examples 12-24

Preparation of Dextran Aldehyde-Polyvinyl Alcohol Acetoacetate Hydrogels Having Different Cure Rates The purpose of these Examples was to demonstrate that the cure rates of the dextran aldehyde-polyvinyl alcohol acetoacetate hydrogels can be controlled by adjusting the equivalent weight of the reactants, the reactant stoichiometry, and the base catalyst content.

Preparation of Hydrogels:

The following solutions were prepared and used to make hydrogels:

3A 25 wt % dextran aldehyde ($M_w$=10 kDa; 48% conv; eq wt=160)
3B 25 wt % dextran aldehyde ($M_w$=10 kDa; 35% conv; eq wt=210)
3C 25 wt % dextran aldehyde ($M_w$=10 kDa; 23% conv; eq wt=330)
3D 19 wt % PVOH acac ($M_w$=31-50 kDa; eq wt=740)+0.50 wt % $Na_2CO_3$
3E 19 wt % PVOH acac ($M_w$=31-50 kDa; eq wt=740)+0.25 wt % $Na_2CO_3$.

The quantities of the two reacting solutions, as indicated in Table 8, were mixed on a microscope slide until the mixture gelled and the gel time was recorded. The results are given in Table 8.

TABLE 8

Cure Times for Hydrogels

| Example | PVOH acac Solution | Vol PVOH acac Solution µL | Dextran Aldehyde Solution | Vol Dextran Aldehyde Solution µL | Acac/ Aldehyde Mole Ratio | Cure time sec |
|---|---|---|---|---|---|---|
| 12 | 3D | 100 | 3A | 20 | 0.8 | 7 |
| 13 | 3D | 100 | 3A | 40 | 0.4 | 8 |
| 14 | 3D | 100 | 3B | 20 | 1.1 | 10 |
| 15 | 3D | 100 | 3B | 40 | 0.6 | 19 |
| 16 | 3D | 100 | 3C | 20 | 1.7 | 17 |
| 17 | 3D | 100 | 3C | 40 | 0.9 | 19 |
| 18 | 3E | 100 | 3A | 20 | 0.8 | 15 |
| 19 | 3E | 100 | 3A | 40 | 0.4 | 19 |
| 20 | 3E | 100 | 3B | 20 | 1.1 | 30 |
| 21 | 3E | 100 | 3B | 40 | 0.6 | 70 |
| 22 | 3E | 100 | 3C | 20 | 1.7 | 30 |
| 23 | 3E | 100 | 3C | 40 | 0.9 | 40 |

As can been seen from the results in Table 8, the cure rate was varied from less than 10 sec to over a minute by adjusting the equivalent weight of the reactants, the reactant stoichiometry, and the base catalyst content. Low equivalent weights, an acac:aldehyde (CHO) mole ratio near 1, and high base concentration all resulted in fast cure times. Conversely, high equivalent weights, off-stoichiometry, and low base catalyst concentration all resulted in longer cure times.

Example 24

Biocompatibility of Dextran Aldehyde-Polyvinyl Alcohol Acetoacetate Hydrogels in Cell Cultures The purpose of this Example was to demonstrate the safety of the dextran aldehyde-polyvinyl alcohol acetoacetate hydrogel in an in vitro test using NIH3T3 human fibroblast cell cultures.

The testing was done using NIH3T3 human fibroblast cell cultures according to ISO10993-5:1999. The NIH3T3 human fibroblast cells were obtained from the American Type Culture Collection (ATCC), Manassas, Va., and were grown in Dulbecco's modified essential medium (DMEM), supplemented with 10% fetal calf serum.

An NIH3T3 human fibroblast cell culture was challenged with a hydrogel made by combining and mixing with a spatula 100 µL of 20 wt % PVOH acac ($M_w$=31-50 kDa; eq wt=600) containing 0.25 wt % sodium carbonate and 20 µL of 25 wt % dextran aldehyde ($M_w$=10 kDa; 48% conv; eq wt=160) in the plate wells of a polystyrene 6-well culture plate. The hydrogel was coated such that about one fourth of the well bottom was covered. The plate was sterilized under UV light and seeded with 50,000-100,000 NIH3T3 cells per well. The cells grew normally confluent and coated the well bottom, growing up to the edges of the hydrogel; however, they did not overgrow the hydrogel. This result demonstrates a lack of pronounced cytotoxicity on the part of the dextran aldehyde-PVOH acac hydrogel.

Example 25

In Vitro Biocompatibility Testing of Dextran Aldehyde-Polyvinyl Alcohol Acetoacetate Hydrogels The purpose of this Example was to demonstrate the non-inflammatory response produced by the dextran aldehyde-PVOH acac hydrogel in an in vitro test using J774 Macrophage.

The testing was done using J774 Macrophage cultures according to ISO10993-5:1999. The J774 Macrophage cells were obtained from ATCC and were grown in DMEM supplemented with 10% fetal bovine serum.

A J774 mouse peritoneal macrophage cell culture was challenged with a hydrogel made by combining and mixing with a spatula 100 µL of 20 wt % PVOH acac ($M_w$=31-50 kDa; eq wt=600) containing 0.25 wt % sodium carbonate and 20 µL of 25 wt % dextran aldehyde ($M_w$=10 kDa; 48% conv; eq wt=160) in the plate wells of a polystyrene 6-well culture plate. The hydrogel was coated such that about one fourth of the well bottom was covered. The plate was sterilized under UV light and seeded with J774 cells. The cell culture was then analyzed for TNF-α, an indicator of inflammatory response, using an ELISA assay, as described by Lara et al. (*Journal of Dental Research* 82(6):460-465, 2003). The TNF-α titer was similar to the negative control (a blank well), indicating the non-inflammatory nature of the dextran aldehyde-PVOH acac hydrogel.

Examples 26-34

Preparation of Dextran Aldehyde-Polyvinyl Alcohol Acetoacetate Hydrogels with Higher Molecular Weight Dextran Aldehyde The purpose of these Examples was to prepare and characterize dextran aldehyde-polyvinyl alcohol acetoacetate hydrogels that were made with higher molecular weight dextran aldehyde (i.e. $M_w$=40,000).

Preparation of Hydrogels:

The following solutions were prepared and used to make hydrogels:
 4A 15 wt % dextran aldehyde ($M_w$=40 kDa; 50% conv; eq wt=160)
 4B 20 wt % dextran aldehyde ($M_w$=40 kDa; 20% conv; eq wt=360)
 4C 19 wt % PVOH acac ($M_w$=31-50 kDa; eq wt=600)+0.25 wt % $Na_2CO_3$
 4D 19 wt % PVOH acac ($M_w$=31-50 kDa; eq wt=740)+ 0.25 wt % $Na_2CO_3$
 4E 19 wt % PVOH acac ($M_w$=31-50 kDa; eq wt=925)+0.25 wt % $Na_2CO_3$.

Hydrogel disks were prepared using the method described in Examples 3-11 using the solutions given in Table 9. Gel times were typically 20 sec or less.

TABLE 9

Solutions Used to Prepare Hydrogels

| Example | Dextran Aldehyde Solution | Vol Dextran Aldehyde Solution µL | PVOH acac Solution | Vol PVOH acac Solution µL | Acac/Aldehyde Mole Ratio |
|---|---|---|---|---|---|
| 26 | 4A | 100 | 4C | 300 | 1.0 |
| 27 | 4B | 60 | 4C | 300 | 2.9 |
| 28 | 4B | 150 | 4C | 250 | 1.0 |
| 29 | 4A | 100 | 4D | 300 | 0.8 |
| 30 | 4B | 60 | 4D | 300 | 2.4 |
| 31 | 4B | 150 | 4D | 250 | 0.8 |
| 32 | 4A | 100 | 4E | 300 | 0.7 |
| 33 | 4B | 60 | 4E | 300 | 1.9 |
| 34 | 4B | 150 | 4E | 250 | 0.6 |

Characterization of Hydrogel Disk Properties:

The mechanical properties and the swelling properties of the hydrogel disks were evaluated using the tests described in Examples 1 and 2. The results of the testing are provided in Tables 10 and 11.

TABLE 10

Results of Mechanical Tests of Hydrogels

| Example | Appearance of Hydrogel | Snap on Bending | Stretch to Break |
|---|---|---|---|
| 26 | Firm rubber | 90° | <10% |
| 27 | Firm rubber | >90° | >10% |
| 28 | Stiff rubber | 90° | <10% |
| 29 | Firm rubber | >90° | 10% |
| 30 | Firm rubber | 180° | 10% |
| 31 | Firm rubber | 180° | 10% |
| 32 | Firm rubber | 90° | 10% |
| 33 | Soft rubber | 180° | 10% |
| 34 | Firm rubber | 180° | 10% |

TABLE 11

Results of Swelling Tests

| Example | Appearance | Stretch to Break | Snap on Bending | Water Swell | Q |
|---|---|---|---|---|---|
| 26 | Firm rubber | 10% | >90° | 0.33 | 6.0 |
| 27 | Firm rubber | 10% | >90° | 0.83 | 8.3 |
| 28 | Stiff rubber | 10% | >90° | 0.24 | 5.5 |
| 29 | Firm rubber | <10% | >90° | 0.38 | 6.8 |
| 30 | Soft rubber | 10% | 180° | 1.05 | 9.3 |
| 31 | Firm rubber | 10% | >90° | 0.51 | 7.2 |
| 32 | Firm rubber | 10% | >90° | 0.54 | 8.0 |
| 33 | Soft rubber | 10% | 180° | 1.00 | 9.0 |
| 34 | Firm rubber | 10% | 180° | 0.75 | 8.3 |

The hydrogel disks were then soaked in phosphate buffer (pH=7.4) for 7 days and the mechanical properties were retested. The results of the testing are given in Table 12.

TABLE 12

Results of Mechanical Tests of Soaked Hydrogels

| Example | Appearance of Hydrogel | Snap on Bending | Stretch to Break |
|---|---|---|---|
| 26 | Firm rubber | >90° | <10% |
| 27 | Soft rubber | 180° | 10% |
| 28 | Firm rubber | 180° | 10% |
| 29 | Firm rubber | 180° | <10% |
| 30 | Soft rubber | 180° | 10% |
| 31 | Soft rubber | 180° | 25% |
| 32 | Soft rubber | 180° | 25% |
| 33 | Soft rubber | 180° | 25% |
| 34 | Soft rubber | 180° | 25% |

The greater extension to break in Examples 31-34, as compared with Examples 8-11, demonstrates the greater hydrogel strength on prolonged soaking conferred by the higher molecular weight dextran aldehyde used in Examples 31-34.

Examples 35-37

Preparation of Dextran Aldehyde-Polyvinyl Alcohol Acetoacetate Hydrogels Containing Linear Polyether Termonomer The purpose of these Examples was to prepare and characterize dextran aldehyde-polyvinyl alcohol acetoacetate hydrogels containing linear polyether termonomer.
Preparation of Linear Ethylene Glycol-Propylene Glycol-Ethylene Glycol Block Polyether Acetoacetate:
A solution of 15 g of poly(ethylene glycol-b-propylene glycol-b-ethylene glycol) diol ($M_n$ approximately 1800; Aldrich #43,541-4; approximately 50 wt % EO) in 50 mL of toluene was prepared and then dried by filtering through 40 g of activity 1 basic alumina under nitrogen. The alumina was then washed by passing through 20 mL more toluene using vacuum. The combined filtrate was placed in a rotary evaporator in a boiling water bath and the solvent was quickly evaporated. The resulting material was held under high vacuum in the water bath with a nitrogen bleed through a 20-gauge syringe needle for 1 h to yield 9.5 g of dry polyether diol.

A solution of 9.0 g (9.0 mmol OH) of poly(ethylene glycol-b-propylene glycol-b-ethylene glycol) diol and 20 mg of N,N-4-dimethylaminopyridine was made in 40 mL of anhydrous tetrahydrofuran (THF) in a 200-mL round bottom flask under nitrogen. The solution was stirred and 2.0 mL (2.2 g; 26 mmol) of 97% diketene (Aldrich #302058) was added. The dark orange solution was stirred in an 80° C. oil bath for 3 h. Then, 2 mL (60 mmol) of methanol was added and the mixture was stirred for 15 min and then quickly filtered through a 0.5-inch (1.3 cm) bed of activity 1 basic alumina. The filtrate was filtered through a micron filter to remove haze and was then placed in a rotary evaporator in a hot water bath and held under high vacuum under a nitrogen stream from a 20-gauge syringe needle for 1.5 h to yield 9.1 g of polyether acetoacetate as a clear red-brown liquid.

1H NMR (CDCl$_3$) 1.14 ppm (m, 52H, backbone PO CH$_3$); 1.24 (m, 1H, terminal PO CH$_3$); 2.27 (s, 6.6H, acac CH$_3$; theory=6H for 2 acac ends); 3.3-3.8 (m, approximately 53H, backbone CH and CH$_2$); 4.30 (t, 3.6H, terminal EO CH$_2$; theory=3.6H for 90% of 2 acac ends); 5.08 (quintet, 0.15H, terminal PO CH); essentially 100% conversion. Mn of approximately 1920; eq wt=960. There are about 25 EO units to 17 PO units per molecule; ratio of EO:PO end groups=0.92:0.08.

Preparation of Hydrogels:
The following solutions were prepared and used to make hydrogels:
5A 25 wt % dextran aldehyde ($M_w$=10 kDa; 50% conv; eq wt=160)
5B 20 wt % poly(ethylene glycol-propylene glycol-ethylene glycol) diol acetoacetate, prepared as described above. This mixture was not a solution; it was an aqueous suspension that had to be stirred continuously.
5C 19 wt % PVOH acac ($M_w$=31-50 kDa; eq wt=600)+0.25 wt % Na$_2$CO$_3$
5D 19 wt % PVOH acac ($M_w$=31-50 kDa; eq wt=740)+0.25 wt % Na$_2$CO$_3$
5E 19 wt % PVOH acac ($M_w$=31-50 kDa; eq wt=925)+0.25 wt % Na$_2$CO$_3$ Hydrogel disks were prepared using the method described in Examples 3-11 using the solutions given in Table 13.

TABLE 13

Solutions Used to Prepare Hydrogels

| Example | Dextran Aldehyde Solution | Vol Dextran Aldehyde Solution μL | PVOH acac Solution | Vol PVOH acac Solution μL | Polyether acac Solution | Vol Polyether acac Solution μL |
|---|---|---|---|---|---|---|
| 35 | 5A | 150 | 5C | 300 | 5B | 100 |
| 36 | 5A | 120 | 5D | 300 | 5B | 100 |
| 37 | 5A | 100 | 5E | 300 | 5B | 100 |

Characterization of Hydrogel Disk Properties:

The mechanical properties and the swelling properties of the hydrogel disks were evaluated using the tests described in Examples 1 and 2. The results of the testing are provided in Tables 14 and 15.

TABLE 14

Results of Mechanical Tests of Hydrogels

| Example | Appearance of Hydrogel | Snap on Bending | Stretch to Break |
|---|---|---|---|
| 35 | Firm rubber | <90° | <10% |
| 36 | Firm rubber | 90° | <10% |
| 37 | Firm rubber | 90° | <10% |

TABLE 15

Results of Swelling Tests

| Example | Appearance | Stretch to Break | Snap on Bending | Water Swell | Q |
|---|---|---|---|---|---|
| 35 | Soft rubber | <10% | <90° | 0.11 | 4.7 |
| 36 | Soft rubber | <10% | 90° | 0.31 | 6.2 |
| 37 | Soft rubber | <10% | 180° | 0.49 | 7.2 |

The hydrogel disks were then soaked in phosphate buffer (pH=7.4) for 11 days and the mechanical properties were retested. The results of the testing are given in Table 16.

TABLE 16

Results of Mechanical Tests of Soaked Hydrogels

| Example | Appearance of Hydrogel | Snap on Bending | Stretch to Break |
|---|---|---|---|
| 35 | Stiff rubber | 90° | <10% |
| 36 | Firm rubber | >90° | 10% |
| 37 | Firm rubber | >90° | 10% |

The results show that inclusion of the hydrophobic linear polyether acetoacetate reduced swelling values of the hydrogels of Examples 35, 36, and 37 relative to the comparable hydrogels of Examples 3, 6, and 9, respectively. This demonstrates that hydrogel persistence in the body can potentially be modulated by inclusion of hydrophobic termonomers.

Examples 38-40

Formation of Dextran Aldehyde-Polyvinyl Alcohol Acetoacetate Hydrogels Containing Star Polyether Termonomer The purpose of these Examples was to prepare and characterize dextran aldehyde-polyvinyl alcohol acetoacetate hydrogels containing linear star polyether termonomer.

Preparation of 4-Arm Star Polyethylene Glycol Acetoacetate:

A solution of 3.0 g of 4-armed star polyethylene glycol (PEG) (1.2 mmol OH; $M_n$=10,000; Shearwater Polymers Inc., now known as Nektar™ Transforming Therapeutics, Huntsville, Ala.) and 22 mg of 4-dimethylaminopyridine in 20 mL of THF in a 50-mL round bottom flask with condenser was stirred under nitrogen with 1.0 mL (13 mmol) 97% diketene in an oil bath at 70° C. for 3 h. The solution was added to 200 mL of ether and chilled in an ice bath. The precipitate was vacuum filtered, washed three times with 100 mL portions of ether, and dried under vacuum under a nitrogen blanket to yield 3.07 g of tan star PEG tetraacetoacetate.

H NMR (CDCl$_3$): 2.27 ppm (s, 2.7H, acac CH$_3$); 3.4-3.8 (s/m, 220H, PEO chain and ends); 4.30 (t, 2H, —OCH$_2$CH$_2$O-acac).

According to the terminal PEO methylene integral, the PEG appears to be completely functionalized; eq wt=2580. The product was taken up in water and filtered to remove insoluble dihydroacetic acid (a diketene byproduct).

Preparation of Hydrogels:

The following solutions were prepared and used to make hydrogels:

6A 25 wt % dextran aldehyde ($M_w$=10 kDa; 50% conv; eq wt=160)

6B 20 wt % star poly(ethylene glycol) tetraacetoacetate prepared as described above 6C 19 wt % PVOH acac ($M_w$=31-50 kDa; eq wt=600)+ 0.25 wt % Na$_2$CO$_3$ 6D 19 wt % PVOH acac ($M_w$=31-50 kDa; eq wt=740)+ 0.25 wt % Na$_2$CO$_3$ 6E 19 wt % PVOH acac ($M_w$=31-50 kDa; eq wt=925)+0.25 wt % Na$_2$CO$_3$ Hydrogel disks were prepared using the method described in Examples 3-11 using the solutions given in Table 17.

TABLE 17

Solutions Used to Prepare Hydrogels

| Example | Dextran Aldehyde Solution | Vol Dextran Aldehyde Solution μL | PVOH acac Solution | Vol PVOH acac Solution μL | Star PEG acac Solution | Vol Star PEG acac Solution μL |
|---|---|---|---|---|---|---|
| 38 | 6A | 150 | 6C | 300 | 6B | 100 |
| 39 | 6A | 120 | 6D | 300 | 6B | 100 |
| 40 | 6A | 100 | 6E | 300 | 6B | 100 |

Characterization of Hydrogel Disk Properties:

The mechanical properties and the swelling properties of the hydrogel disks were evaluated using the tests described in Examples 1 and 2. The results of the testing are provided in Tables 18 and 19.

TABLE 18

Results of Mechanical Tests of Hydrogels

| Example | Appearance of Hydrogel | Snap on Bending | Stretch to Break |
|---|---|---|---|
| 38 | Stiff rubber | 90° | <10% |
| 39 | Soft rubber | >90° | 10% |
| 40 | Soft rubber | >90° | >10% |

TABLE 19

Results of Swelling Tests

| Example | Appearance | Stretch to Break | Snap on Bending | Water Swell | Q |
|---|---|---|---|---|---|
| 38 | Firm rubber | <10% | 90° | 0.28 | 6.0 |
| 39 | Soft rubber | <10% | 90° | 0.66 | 8.3 |
| 40 | Soft rubber | 10% | 180° | 1.28 | 11.3 |

The hydrogel disks were then soaked in phosphate buffer (pH=7.4) for 10 days and the mechanical properties were retested. The results of the testing are given in Table 20.

TABLE 20

Results of Mechanical Tests of Soaked Hydrogels

| Example | Appearance of Hydrogel | Snap on Bending | Stretch to Break |
|---|---|---|---|
| 38 | Firm rubber | 180° | <10% |
| 39 | Soft rubber | 180° did not break | >10% |
| 40 | Soft rubber | 180° | Beginning to disintegrate |

The results show that inclusion of the hydrophilic star polyether acetoacetate increased swelling values and hydrolytic degradation rates of the hydrogels of Examples 38, 39, and 40 relative to the comparable hydrogels of Examples 3, 6 and 9, respectively. This demonstrates that hydrogel persistence in the body can potentially be modulated by inclusion of hydrophilic termonomers.

Examples 41-47

Sealing an Incision in an Ex Vivo Swine Uterine Horn Using Various Combinations of Dextran Aldehyde and Polyvinyl Alcohol Acetoacetate The purpose of these Examples was to demonstrate the sealing of an incision in a swine uterine horn using various combinations of dextran aldehyde and polyvinyl alcohol acetoacetate.

The following solutions were prepared and used to seal the incision in a swine uterine horn:

7A 15 wt % dextran aldehyde ($M_w$=40 kDa; 20% conv; eq wt=360)

7B 15 wt % dextran aldehyde ($M_w$=40 kDa; 50% conv; eq wt=150)

7C 20 wt % PVOH acac ($M_w$=31-50 kDa; eq wt=490)+ 0.25 wt % $Na_2CO_3$ 7D 20 wt % PVOH acac ($M_w$=31-50 kDa; eq wt=600)+ 0.25 wt % $Na_2CO_3$ A 1-cm scalpel cut was made laterally in an approximately 2-inch (5-cm) section of clean, fresh, damp swine uterine horn, obtained from a local abattoir. A metal nozzle with a feed line for water from a syringe pump was inserted into one end of the uterine horn section and the nozzle was secured with a nylon tie. The open end of the uterine horn was then clamped closed with a hemostat. The surface of the damp uterine horn was blotted once with a paper towel to remove gross water droplets and the dextran aldehyde solution and the PVOH acac solution (as indicated in Table 21) were applied over the incision using a simple two-syringe Y-mixer with a 13-stage static mixing tip (ConProtec, Inc., Salem, N.H.). After application, the adhesive patch was allowed to cure at room temperature for 2 to 3 min. Then, the sealed uterine horn was pressurized with water from the syringe pump (about 0.1 psig/3 sec; (0.7 kPa/3 sec)) until the adhesive seal began to leak water, at which point the pressure and the failure mode were recorded. In terms of failure mode, an adhesive failure was characterized by water leaking underneath the adhesive to the edge. In a cohesive failure, the water penetrated the hydrogel itself rather than leaking under it. The results are given in Table 21.

TABLE 21

Results of Sealing an Incision in Swine Uterine Horn

| Example | PVOH acac | Dextran Aldehyde | CHO: acac | Vol ratio PVOH:Dextran Aldehyde | Failure | Burst psi (kPa) |
|---|---|---|---|---|---|---|
| 41 | 7C | 7A | 0.3 | 3.3:1 | Adhesion | 0.3 (2.1) |
| 42 | 7C | 7A | 0.3 | 3.3:1 | Adhesion | 0.3 (2.1) |
| 43 | 7C | 7A | 0.3 | 3.3:1 | Adhesion | 1.0 (6.9) |
| 44 | 7D | 7B | 0.8 | 3.3:1 | Adhesion | 0.5 (3.4) |
| 45 | 7D | 7B | 0.8 | 3.3:1 | Adhesion | 0.7 (4.8) |
| 46 | 7D | 7B | 0.8 | 3.3:1 | Adhesion | 1.1 (7.6) |
| 47 | 7D | 7B | 3.0 | 1:1 | Adhesion | 0.8 (5.5) |

The results demonstrate that the dextran aldehyde-PVOH acac hydrogel functions as a bioadhesive to seal an incision in swine uterine horn. Higher burst pressures on average were obtained with higher aldehyde-content dextran aldehyde, as shown in Examples 44-47.

Examples 48-60

Sealing an Incision in an Ex Vivo Swine Uterine Horn Using Dextran Aldehydes with Different Molecular Weights and Polyvinyl Alcohol Acetoacetate with Various Base Catalysts The purpose of these Examples was to demonstrate the effect of the molecular weight of the dextran aldehyde and the base catalyst used on the sealing of an incision in a swine uterine horn. Dextran aldehydes having weight-average molecular weights of 10, 20, and 40 kDa were used. The base catalysts used were sodium carbonate, sodium bicarbonate, and triethanolamine.

The following solutions were prepared and used to seal the incision in swine uterine horn:

8A 25 wt % dextran aldehyde ($M_w$=10 kDa; 48% conv; eq wt=160)

8B 25 wt % dextran aldehyde ($M_w$=20 kDa; 50% conv; eq wt=160)

8C 15 wt % dextran aldehyde ($M_w$=40 kDa; 50% conv; eq wt=160)

8D 20 wt % PVOH acac ($M_w$=31-50 kDa; eq wt=490)+ 0.25 wt % Na2CO3

8E 20 wt % PVOH acac ($M_w$=31-50 kDa; eq wt=575)+0.25 wt % Na2CO3

8F 20 wt % PVOH acac ($M_w$=31-50 kDa; eq wt=575)+0.25 wt % NaHCO3

8G 25 wt % dextran aldehyde ($M_w$=20 kDa; 50% conv; eq wt=160)+5 wt % triethanolamine 8H 20 wt % PVOH acac ($M_w$=31-50 kDa; eq wt=490).

The method used to seal the incision in swine uterine horn was the same as described in Examples 41-47 using the combination of solutions given in Table 22. The results obtained are shown in Table 22.

TABLE 22

Results of Sealing an Incision in Uterine Horn

| Example | PVOH acac | Dextran Aldehyde | CHO: acac | Vol ratio PVOH:Dextran Aldehyde | Failure | Burst psi (kPa) |
|---|---|---|---|---|---|---|
| 48 | 8E | 8A | 4.5 | 1:1 | Adhesion | 1.1 (7.6) |
| 49 | 8E | 8A | 4.5 | 1:1 | Cohesion | 1.4 (9.6) |
| 50 | 8D | 8B | 1.2 | 3.3:1 | Cohesion | 0.9 (6.2) |
| 51 | 8D | 8B | 1.2 | 3.3:1 | Cohesion | 1.2 (8.3) |

TABLE 22-continued

Results of Sealing an Incision in Uterine Horn

| Example | PVOH acac | Dextran Aldehyde | CHO: acac | Vol ratio PVOH:Dextran Aldehyde | Failure | Burst psi (kPa) |
|---|---|---|---|---|---|---|
| 52 | 8D | 8B | 1.2 | 1:1 | Cohesion | 1.1 (7.6) |
| 53 | 8D | 8B | 1.2 | 1:1 | Cohesion | 1.0 (6.9) |
| 54 | 8E | 8C | 2.9 | 1:1 | Cohesion | 1.3 (9.0) |
| 55 | 8F | 8C | 2.9 | 1:1 | Cohesion | 0.5 (3.4) |
| 56 | 8F | 8C | 2.9 | 1:1 | Cohesion | 1.0 (6.9) |
| 57 | 8H | 8G | 3.8 | 1:1 | Adhesion | 1.1 (7.6) |
| 58 | 8H | 8G | 3.8 | 1:1 | Adhesion | 1.0 (6.9) |
| 59 | 8H | 8G | 3.8 | 1:1 | Cohesion | 1.4 (9.6) |
| 60 | 8H | 8G | 3.8 | 1:1 | Adhesion | 1.2 (8.3) |

These results show that the molecular weight of the dextran aldehyde does not have much effect on the adhesive strength, as measured by the burst pressure (shown in Examples 48-54). However, the higher molecular weight (i.e., $M_w$=40 kDa) dextran aldehyde does compensate for lower solids content (15 wt %), as shown in Example 54. The results also demonstrate, that despite its mild basicity, sodium bicarbonate (NaHCO3) is a satisfactory base catalyst for the gelation of dextran aldehyde and polyvinyl alcohol acetoacetate, as shown in Examples 55 and 56. Additionally, the organic tertiary amine triethanolamine functions well as a base catalyst for gelation of dextran aldehyde and polyvinyl alcohol acetoacetate, as shown in Examples 57-60.

Examples 61-79

Gelation of Dextran Aldehyde and Polyvinyl Alcohol Acetoacetate with Various Base Catalysts The purpose of these Examples was to demonstrate the effect of the pKa of the conjugate acid (base strength) of various base catalysts on the rate of crosslinking of a mixture of dextran aldehyde and polyvinyl alcohol acetoacetate. Dextran aldehyde with 50% conversion and having a weight-average molecular weight of 10 kDa and polyvinyl alcohol acetoacetate having an equivalent weight of 500 and a weight-average molecular weight of 31-50 kDa were used. Both solutions were 20 wt % and the solutions were combined in a 1:1 volume ratio before adding the catalytic base, either as an aqueous solution or (in the case of certain organic bases) as a neat liquid (Examples 76, 77, and 79). The results are shown in Table 23. Examples 63, 64, and 74 are comparative Examples.

TABLE 23

Gelation Rates vs Base pKa

| Ex | Base Type and Concentration | Base pKa | Base Vol | 20 wt % PVOH acac EW = 500 | 20 wt % Dex CHO EW = 160 | Cure Time |
|---|---|---|---|---|---|---|
| 61 | trisodium phosphate 10% | 12.7 | 10 µL | 50 µL | 50 µL | 5 sec |
| 62 | dibasic potassium phosphate 10% | 7.2 | 10 µL | 50 µL | 50 µL | 40 sec |
| 63 | sodium dihydrogen phosphate 10% | 2.1 | 10 µL | 50 µL | 50 µL | no gelation in 10 min |
| 64 | calcium pyrophosphate 10% | 9 | 10 µL suspension | 50 µL | 50 µL | no gelation in 10 min |
| 65 | NaOH 10% | 14 | 10 µL | 50 µL | 50 µL | 5 sec |
| 66 | ammonium hydroxide 10% | 9.2 | 10 µL | 50 µL | 50 µL | 4 sec |
| 67 | sodium carbonate 10% | 10.3 | 10 µL | 50 µL | 50 µL | 5 sec |
| 68 | sodium carbonate 5% | 10.3 | 10 µL | 50 µL | 50 µL | 5 sec |
| 69 | sodium bicarbonate 7% | 6.3 | 10 µL | 50 µL | 50 µL | 20 sec |
| 70 | calcium carbonate 10% | 10 | 10 µL suspension | 50 µL | 50 µL | 90 sec |
| 71 | sodium tetraborate 10% | 12 | 10 µL | 50 µL | 50 µL | 3 sec |
| 72 | sodium sulfite 10% | 6.9 | 10 µL | 50 µL | 50 µL | 5 sec |
| 73 | sodium methylthiolate 10% | 12 | 10 µL | 50 µL | 50 µL | 5 sec |
| 74 | sodium acetate 10% | 4.8 | 10 µL | 50 µL | 50 µL | no gelation in 10 min |
| 75 | tetrasodium ethylenediaminetetraacetic acid 10% | 11 | 10 µL | 50 µL | 50 µL | 6 sec |
| 76 | diisopropylamine | 11.1 | 5 µL neat | 50 µL | 50 µL | 3 sec |
| 77 | triethylamine | 11 | 5 µL neat | 50 µL | 50 µL | 6 sec |

TABLE 23-continued

Gelation Rates vs Base pKa

| Ex | Base Type and Concentration | Base pKa | Base Vol | 20 wt % PVOH acac EW = 500 | 20 wt % Dex CHO EW = 160 | Cure Time |
|---|---|---|---|---|---|---|
| 78 | imidazole 10% | 7 | 10 µL | 50 µL | 50 µL | 20 sec |
| 79 | pyridine | 5.2 | 5 µL neat | 50 µL | 50 µL | 150 sec |

The pKa of the methylene protons of the acetoacetate group is about 11. Bases for which the conjugate acid pKa is 5 or less are poor crosslinking catalysts because the base strength is too low to form a significant concentration of acetoacetate anion to condense with the aldehyde groups on the oxidized polysaccharide. Use of bases for which the conjugate acid pKa is greater than 7 results in fast crosslinking. Therefore, the crosslinking rate can be modulated by varying base strength. In cases of base insolubility (Examples 64 and 70), the rate of anion generation and crosslinking is slow despite good base strength because the base concentration in solution is low. Using a base of low solubility, or a low concentration of a soluble base, also constitutes a method of modulating crosslinking rate in addition to simply varying base strength. While all the soluble strong bases effectively catalyze crosslinking, it must be appreciated that not all strong bases are appropriate for use in living systems due to their potential toxicity. The carbonate and phosphate salts are preferable for use in biological applications.

What is claimed is:

1. A method for sealing an orifice in tissue in the body of a living animal comprising:
    applying to the orifice
    (a) a first aqueous solution comprising from about 5% to about 40% by weight of a polysaccharide that has been oxidized to provide an oxidized polysaccharide that contains aldehyde groups, said polysaccharide having a molecular weight of about 1,000 to about 1,000,000 Daltons, and said oxidized polysaccharide having an equivalent weight per aldehyde group of about 90 to about 1500 Daltons, such that the oxidized polysaccharide has on average more than two aldehyde groups, followed by
    (b) a second aqueous solution comprising from about 5% to about 40% by weight of poly(vinyl alcohol) that has been derivatized to provide a derivatized poly(vinyl alcohol) that contains acetoacetate groups, said poly(vinyl alcohol) having a molecular weight of less than or equal to about 100,000 Daltons, and said derivatized poly(vinyl alcohol) having an equivalent weight per acetoacetate group of about 100 to about 2000 Daltons, such that the derivatized poly(vinyl alcohol) has on average more than two acetoacetate groups, or applying the second aqueous solution followed by the first aqueous solution and mixing the first and second aqueous solutions on the orifice, or premixing the first and second aqueous solutions and applying the resulting mixture to the orifice before the resulting mixture completely cures, thereby forming on said orifice a resorbable adhesive hydrogel, and allowing the hydrogel to remain on said orifice until said hydrogel is resorbed;
    provided that:
    (i) at least one of the first aqueous solution or the second aqueous solution further comprises a base catalyst; or
    (ii) a base catalyst is applied to the orifice as a neat liquid or as part of a third aqueous solution, and said neat liquid or third aqueous solution is mixed with both the first aqueous and second aqueous solutions on the orifice or said neat liquid or third aqueous solution is premixed with both the first and second aqueous solutions, and the resulting mixture is subsequently applied to the orifice before the resulting mixture completely cures; or
    (iii) a combination of (i) and (ii);
    wherein the polysaccharide is selected from the group consisting of dextran, chitin, starch, agar, cellulose and hyaluronic acid.

2. A method for bonding at least two anatomical sites together comprising:
    applying to at least one of the at least two anatomical sites
    (a) a first aqueous solution comprising from about 5% to about 40% by weight of a polysaccharide that has been oxidized to provide an oxidized polysaccharide that contains aldehyde groups, said polysaccharide having a molecular weight of about 1,000 to about 1,000,000 Daltons, and said oxidized polysaccharide having an equivalent weight per aldehyde group of about 90 to about 1500 Daltons, such that the oxidized polysaccharide has on average more than two aldehyde groups, followed by
    (b) a second aqueous solution comprising from about 5% to about 40% by weight of poly(vinyl alcohol) that has been derivatized to provide a derivatized poly(vinyl alcohol) that contains acetoacetate groups, said poly(vinyl alcohol) having a molecular weight of less than or equal to about 100,000 Daltons, and said derivatized poly(vinyl alcohol) having an equivalent weight per acetoacetate group of about 100 to about 2000 Daltons, such that the derivatized poly(vinyl alcohol) has on average more than two acetoacetate groups, or
    applying the second aqueous solution followed by the first aqueous solution and mixing the first and second aqueous solutions on the at least one site, or premixing the first and second aqueous solutions and applying the resulting mixture to the at least one anatomical site before the resulting mixture completely cures,
    and contacting the at least two anatomical sites together;
    provided that:
    (i) at least one of the first aqueous solution or the second aqueous solution further comprises a base catalyst; or
    (ii) a base catalyst is applied to the at least one site as a neat liquid or as part of a third aqueous solution, and said neat liquid or third aqueous solution is mixed with both the first aqueous and second aqueous solutions on said at least one site or said neat liquid or third aqueous solution is premixed with both the first and second aqueous solutions, and the resulting mixture is subsequently applied to the at least one site before the resulting mixture completely cures; or (iii) a combination of (i) and (ii);

wherein the polysaccharide is selected from the group consisting of dextran, chitin, starch, agar, cellulose and hyaluronic acid.

3. The method according to claim 1 or claim 2 wherein the molecular weight of the polysaccharide is from about 3,000 to about 250,000 Daltons.

4. The method according to claim 1 or claim 2 wherein the first aqueous solution, the second aqueous solution, and the neat liquid or third aqueous solution, if present, are sterilized.

5. The method according to claim 1 or claim 2 wherein the polysaccharide is dextran.

6. The method according to claim 5 wherein said poly(vinyl alcohol) has a weight-average molecular weight in the range of from about 10,000 Daltons to about 50,000 Daltons.

7. The method according to claim 5 wherein said poly(vinyl alcohol) has a weight-average molecular weight in the range of from about 30,000 Daltons to about 50,000 Daltons.

8. The method according to claim 1 or claim 2 wherein the base catalyst is selected from the group consisting of sodium carbonate, sodium bicarbonate, trisodium phosphate, dibasic sodium phosphate, tetrasodium ethylenediaminetetraacetic acid, calcium carbonate, potassium carbonate, potassium bicarbonate, tripotassium phosphate, dibasic potassium phosphate, tetrapotassium ethylenediaminetetraacetic acid, triethanolamine and imidazole.

9. The method according to claim 1 or claim 2 wherein the base catalyst is present in at least one of the first aqueous solution, the second aqueous solution, or the third aqueous solution at a concentration of about 0.01% to about 1% by weight relative to the total weight of the solution.

10. The method according to claim 1 or claim 2 wherein at least one of the first aqueous solution, the second aqueous solution, or the third aqueous solution further comprises at least one additive selected from the group consisting of viscosity modifiers, antimicrobials, colorants, healing promoters, surfactants, anti-inflammatory agents, thrombogenic agents, and radio-opaque compounds.

11. The method according to claim 10 wherein the antimicrobial is selected from the group consisting of methylparaben, ethylparaben, propylparaben, butylparaben, cresol, chlorocresol, hydroquinone, sodium benzoate, potassium benzoate, triclosan and chlorhexidine.

12. The method according to claim 10 wherein the colorant is selected from the group consisting of FD&C Violet No. 2, D&C Green No. 6, D&C Green No. 5, and D&C Violet No. 2.

13. The method according to claim 1 or claim 2 wherein at least one of the first aqueous solution, the second aqueous solution, or the third aqueous solution further comprises a pharmaceutical drug or therapeutic agent.

14. The method according to claim 1 or claim 2 wherein the concentration of the oxidized polysaccharide in the first aqueous solution is from about 15% to about 30% by weight.

15. The method according to claim 1 or claim 2 wherein the concentration of the derivatized poly(vinyl alcohol) in the second aqueous solution is from about 15% to about 30% by weight.

16. The method according to claim 1 or claim 2 wherein at least one of the second aqueous solution or the third aqueous solution further comprises a termonomer that has been derivatized with acetoacetate groups.

17. The method according to claim 16 wherein the termonomer is selected from the group consisting of linear polyethers, branched polyethers, water-dispersible hydroxyl-ended linear polyesters, water-dispersible hydroxyl-ended branched polyesters, star polyethers, and partially-esterified poly(vinyl alcohol).

18. The method according to claim 1 further comprising applying to the orifice a fourth aqueous solution comprising a water-dispersible termonomer that has been derivatized with acetoacetate groups, wherein the first and second aqueous solutions and the neat liquid or third aqueous solution if present, and the fourth aqueous solution are applied in any order and are mixed on the orifice, or are premixed and applied to the orifice before the resulting mixture completely cures.

19. The method according to claim 18 wherein the termonomer is selected from the group consisting of linear polyethers, branched polyethers, water-dispersible linear polyesters, water-dispersible branched polyesters, star polyethers, and partially-esterified poly(vinyl alcohol).

20. The method according to claim 2 further comprising applying to the at least one anatomical site a fourth aqueous solution comprising a termonomer that has been derivatized with acetoacetate groups, wherein the first and second aqueous solutions and the neat liquid or third aqueous solution if present, and the fourth aqueous solution are applied in any order and are mixed on the at least one site, or are premixed and applied to the at least one site before the resulting mixture completely cures.

21. The method according to claim 20 wherein the termonomer is selected from the group consisting of linear polyethers, branched polyethers, water-dispersible hydroxyl-ended linear polyesters, water-dispersible hydroxyl-ended branched polyesters, star polyethers, and partially-esterified poly(vinyl alcohol).

22. The method according to claim 18 or claim 20 wherein the fourth aqueous solution is sterilized.

23. The method according to claim 1 or claim 2 wherein the ratio of aldehyde groups of the oxidized polysaccharide of the first aqueous solution to the acetoacetate groups of the derivatized poly(vinyl alcohol) of the second aqueous solution is greater than or equal to 1.

24. The method according to claim 1 wherein the orifice is a wound on the skin and the method is used for treatment of topical wounds.

25. The method according to claim 1 wherein the orifice is an incision, suture, or staple in the intestine or a blood vessel and the method is used in an anastomosis procedure.

26. The method according to claim 1 wherein the orifice is a surgical incision in the cornea and the method is used to seal the incision.

27. The method of claim 1 wherein at least one of the first aqueous solution, the second aqueous solution, or the third aqueous solution further comprises a pharmaceutical drug or therapeutic agent and the method is used for drug delivery to an anatomical site.

* * * * *

UNITED STATES PATENT AND TRADEMARK OFFICE
CERTIFICATE OF CORRECTION

| | | |
|---|---|---|
| PATENT NO. | : 8,679,537 B2 | Page 1 of 1 |
| APPLICATION NO. | : 11/509255 | |
| DATED | : March 25, 2014 | |
| INVENTOR(S) | : Samuel David Arthur | |

It is certified that error appears in the above-identified patent and that said Letters Patent is hereby corrected as shown below:

Title Page, item (73), should read

Actamax Surgical Materials, LLC

Signed and Sealed this
First Day of July, 2014

Michelle K. Lee
*Deputy Director of the United States Patent and Trademark Office*